US008765915B2

(12) United States Patent
Weimer et al.

(10) Patent No.: US 8,765,915 B2
(45) Date of Patent: *Jul. 1, 2014

(54) MODIFIED COAGULATION FACTOR VIIA WITH EXTENDED HALF-LIFE

(75) Inventors: Thomas Weimer, Gladenbach (DE); Stefan Schulte, Marburg (DE); Ulrich Kronthaler, Marburg (DE); Wiegand Lang, Cölbe (DE); Uwe Liebing, Cölbe (DE); Wilfried Wormsbächer, Kirchhain (DE)

(73) Assignee: CSL Behring GmbH, Marburg (DE)

( * ) Notice: Subject to any disclaimer, the term of this patent is extended or adjusted under 35 U.S.C. 154(b) by 467 days.

This patent is subject to a terminal disclaimer.

(21) Appl. No.: 12/223,616

(22) PCT Filed: Feb. 3, 2007

(86) PCT No.: PCT/EP2007/000937
§ 371 (c)(1),
(2), (4) Date: Aug. 5, 2008

(87) PCT Pub. No.: WO2007/090584
PCT Pub. Date: Aug. 16, 2007

(65) Prior Publication Data
US 2009/0298760 A1 Dec. 3, 2009

(30) Foreign Application Priority Data
Feb. 6, 2006 (EP) .................... 06002359

(51) Int. Cl.
*A61K 38/35* (2006.01)
*A61K 38/38* (2006.01)
*C07K 14/745* (2006.01)
*C07K 14/76* (2006.01)
*C07K 14/765* (2006.01)
*C12N 9/64* (2006.01)
*A61K 38/00* (2006.01)

(52) U.S. Cl.
CPC .............. *C12N 9/6437* (2013.01); *C07K 14/76* (2013.01); *C12Y 304/21021* (2013.01); *A61K 38/00* (2013.01); *C07K 2319/00* (2013.01)
USPC ........... 530/380; 530/384; 530/362; 514/14.3

(58) Field of Classification Search
None
See application file for complete search history.

(56) References Cited

U.S. PATENT DOCUMENTS

| 4,784,950 | A | 11/1988 | Hagen et al. |
| 4,970,300 | A | 11/1990 | Fulton et al. |
| 5,223,408 | A | 6/1993 | Goeddel et al. |
| 5,302,697 | A | 4/1994 | Goodey et al. |
| 5,364,771 | A | 11/1994 | Lollar et al. |
| 5,503,993 | A | 4/1996 | Hayasuke et al. |
| 5,580,560 | A | 12/1996 | Nicolaisen et al. |
| 5,616,474 | A | 4/1997 | Bolotin et al. |
| 5,625,041 | A | 4/1997 | Johnson et al. |
| 5,641,663 | A | 6/1997 | Garvin et al. |
| 5,646,012 | A | 7/1997 | Fleer et al. |
| 5,665,863 | A | 9/1997 | Yeh |
| 5,667,986 | A | 9/1997 | Goodey et al. |
| 5,705,363 | A | 1/1998 | Imakawa |
| 5,714,377 | A | 2/1998 | Tanner et al. |
| 5,766,883 | A | 6/1998 | Ballance et al. |
| 5,766,897 | A | 6/1998 | Braxton |
| 5,876,969 | A | 3/1999 | Fleer et al. |
| 5,959,075 | A | 9/1999 | Lok et al. |
| 5,969,040 | A | 10/1999 | Hallahan et al. |
| 6,087,129 | A | 7/2000 | Newgard et al. |
| 6,110,707 | A | 8/2000 | Newgard et al. |
| 6,114,146 | A | 9/2000 | Herlitschka et al. |
| 6,177,059 | B1 | 1/2001 | Matsuda et al. |
| 6,300,065 | B1 | 10/2001 | Kieke et al. |
| 6,348,327 | B1 | 2/2002 | Gorman et al. |
| 6,403,077 | B1 | 6/2002 | Strom et al. |
| 6,548,653 | B1 * | 4/2003 | Young et al. ................. 536/23.4 |
| 6,686,179 | B2 | 2/2004 | Fleer et al. |
| 6,905,688 | B2 | 6/2005 | Rosen et al. |
| 6,926,898 | B2 | 8/2005 | Rosen et al. |

(Continued)

FOREIGN PATENT DOCUMENTS

| EP | 0 301 670 A1 | 2/1989 |
| EP | 0 319 641 A1 | 6/1989 |
| EP | 0 399 666 A1 | 11/1990 |
| EP | 0 511 912 A1 | 11/1992 |
| EP | 0 711 835 A1 | 5/1996 |
| EP | 0 770 625 B1 | 5/1997 |
| EP | 1 444 986 A1 | 8/2004 |
| EP | 0 624 195 B1 | 9/2004 |
| EP | 1 816 201 A1 | 8/2007 |
| EP | 1 832 599 A2 | 9/2007 |

(Continued)

OTHER PUBLICATIONS

Xue, F., et al. 2004 Nucleic Acids Research 32: W562-W565.*

(Continued)

*Primary Examiner* — Marsha Tsay
(74) *Attorney, Agent, or Firm* — Finnegan, Henderson, Farabow, Garrett & Dunner, LLP

(57) ABSTRACT

The present invention relates to the fields of Factor VII (FVII) and Factor VIIa (FVIIa) albumin linked polypeptides. More specifically, the invention relates to cDNA sequences coding for human Factor VII and Factor VIIa and derivatives genetically fused to a cDNA coding for human serum albumin which may be linked by oligonucleotides which code for intervening peptidic linkers such encoded derivatives exhibiting improved stability and extended functional plasma half-life, recombinant expression vectors containing such cDNA sequences, host cells transformed with such recombinant expression vectors, recombinant polypeptides and derivatives which do have biological activities of the unmodified wild type protein but having improved stability and prolonged shelf-life and processes for the manufacture of such recombinant proteins and their derivatives. The invention also covers a transfer vector for use in human gene therapy, which comprises such modified DNA sequences.

13 Claims, 4 Drawing Sheets

(56) References Cited

U.S. PATENT DOCUMENTS

Figure 3:
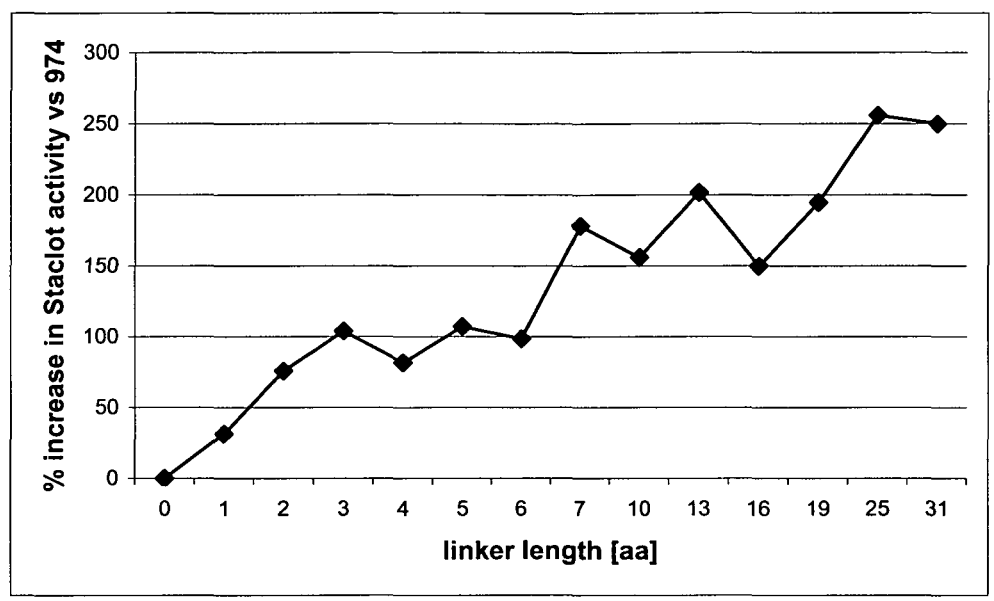

| | | |
|---|---|---|
| 6,946,134 B1 | 9/2005 | Rosen et al. |
| 6,972,322 B2 | 12/2005 | Fleer et al. |
| 6,987,006 B2 | 1/2006 | Fleer et al. |
| 6,989,365 B2 | 1/2006 | Fleer et al. |
| 6,994,857 B2 | 2/2006 | Rosen et al. |
| 7,026,447 B2 | 4/2006 | Rosen et al. |
| 7,041,478 B2 | 5/2006 | Fleer et al. |
| 7,056,701 B2 | 6/2006 | Fleer et al. |
| 7,094,577 B2 | 8/2006 | Fleer et al. |
| 7,122,634 B2 | 10/2006 | Lollar |
| 7,138,371 B2 | 11/2006 | DeFrees et al. |
| 7,141,547 B2 | 11/2006 | Rosen et al. |
| 7,189,690 B2 | 3/2007 | Rosen et al. |
| 7,404,956 B2 | 7/2008 | Peters et al. |
| 7,435,410 B2 | 10/2008 | Fleer et al. |
| 7,482,013 B2 | 1/2009 | Ballance et al. |
| 7,521,424 B2 | 4/2009 | Rosen et al. |
| 7,939,632 B2 | 5/2011 | Metzner et al. |
| 2003/0022308 A1 | 1/2003 | Fleer et al. |
| 2003/0036170 A1 | 2/2003 | Fleer et al. |
| 2003/0036171 A1 | 2/2003 | Fleer et al. |
| 2003/0082747 A1 | 5/2003 | Fleer et al. |
| 2003/0125247 A1 | 7/2003 | Rosen et al. |
| 2003/0139365 A1 | 7/2003 | Lo et al. |
| 2003/0143191 A1 | 7/2003 | Bell et al. |
| 2003/0199043 A1 * | 10/2003 | Ballance et al. .............. 435/69.7 |
| 2003/0219875 A1 | 11/2003 | Rosen et al. |
| 2004/0010134 A1 | 1/2004 | Rosen et al. |
| 2004/0086976 A1 | 5/2004 | Fleer et al. |
| 2004/0086977 A1 | 5/2004 | Fleer et al. |
| 2004/0087778 A1 | 5/2004 | Feige et al. |
| 2005/0054051 A1 | 3/2005 | Rosen et al. |
| 2005/0054570 A1 | 3/2005 | Rosen et al. |
| 2005/0100991 A1 | 5/2005 | Rosen et al. |
| 2005/0113565 A1 | 5/2005 | Klausen et al. |
| 2005/0186664 A1 | 8/2005 | Rosen et al. |
| 2005/0192211 A1 | 9/2005 | Gillies et al. |
| 2005/0244931 A1 | 11/2005 | Rosen et al. |
| 2005/0266532 A1 | 12/2005 | Rosen et al. |
| 2005/0266533 A1 | 12/2005 | Ballance et al. |
| 2006/0014254 A1 | 1/2006 | Haseltine et al. |
| 2006/0084794 A1 | 4/2006 | Rosen et al. |
| 2006/0105429 A1 | 5/2006 | Fleer et al. |
| 2007/0048282 A1 | 3/2007 | Rosen et al. |
| 2008/0167238 A1 | 7/2008 | Rosen et al. |
| 2008/0261877 A1 | 10/2008 | Ballance et al. |
| 2008/0267962 A1 | 10/2008 | Ballance et al. |
| 2008/0269125 A1 | 10/2008 | Ballance et al. |
| 2008/0269126 A1 | 10/2008 | Ballance et al. |
| 2008/0269127 A1 | 10/2008 | Ballance et al. |
| 2009/0042787 A1 | 2/2009 | Metzner et al. |
| 2009/0093402 A1 | 4/2009 | Rosen et al. |
| 2009/0099073 A1 | 4/2009 | Rosen et al. |
| 2009/0298760 A1 | 12/2009 | Weimer et al. |
| 2010/0120664 A1 | 5/2010 | Schulte et al. |
| 2010/0222554 A1 | 9/2010 | Weimer et al. |
| 2011/0189182 A1 | 8/2011 | Metzner et al. |
| 2012/0141415 A1 | 6/2012 | Ballance et al. |
| 2012/0141449 A1 | 6/2012 | Ballance et al. |
| 2012/0252732 A1 | 10/2012 | Ballance et al. |

FOREIGN PATENT DOCUMENTS

| | | |
|---|---|---|
| EP | 1 867 660 A1 | 12/2007 |
| EP | 2 277 889 A2 | 1/2011 |
| FR | 2 719 593 A1 | 11/1995 |
| WO | WO 90/01063 A1 | 2/1990 |
| WO | WO 90/13653 A1 | 11/1990 |
| WO | WO 91/09125 | 6/1991 |
| WO | WO 93/15199 A1 | 8/1993 |
| WO | WO 93/15200 A1 | 8/1993 |
| WO | WO 94/15625 A1 | 7/1994 |
| WO | WO 94/27631 A1 | 12/1994 |
| WO | WO 95/17510 A1 | 6/1995 |
| WO | WO 95/30759 A1 | 11/1995 |
| WO | WO 96/01653 | 1/1996 |
| WO | WO 96/18412 A1 | 6/1996 |
| WO | WO 97/03193 A1 | 1/1997 |
| WO | WO 97/11957 A1 | 4/1997 |
| WO | WO 97/24445 A1 | 7/1997 |
| WO | WO 97/26321 A2 | 7/1997 |
| WO | WO 97/40145 A1 | 10/1997 |
| WO | WO 99/19339 A1 | 4/1999 |
| WO | WO 99/55306 A1 | 11/1999 |
| WO | WO 99/59622 A1 | 11/1999 |
| WO | WO 99/66054 A2 | 12/1999 |
| WO | WO 00/69911 A1 | 11/2000 |
| WO | WO 00/71714 A2 | 11/2000 |
| WO | WO 01/01749 A2 | 1/2001 |
| WO | WO 01/29242 A2 | 4/2001 |
| WO | WO 01/58935 A2 | 8/2001 |
| WO | WO 01/58957 A2 | 8/2001 |
| WO | WO 01/68109 A1 | 9/2001 |
| WO | WO 01/77137 A1 | 10/2001 |
| WO | WO 01/79258 A1 | 10/2001 |
| WO | WO 01/79271 A1 | 10/2001 |
| WO | WO 01/79442 A2 | 10/2001 |
| WO | WO 01/79443 A2 | 10/2001 |
| WO | WO 01/79444 A2 | 10/2001 |
| WO | WO 02/04598 A2 | 1/2002 |
| WO | WO 02/04598 A3 | 1/2002 |
| WO | WO 02/29025 A3 | 4/2002 |
| WO | WO 02/32461 A2 | 4/2002 |
| WO | WO 02/46227 A2 | 6/2002 |
| WO | WO 02/060951 A2 | 8/2002 |
| WO | WO 02/072023 A2 | 9/2002 |
| WO | WO 02/097038 A2 | 12/2002 |
| WO | WO 02/103024 A2 | 12/2002 |
| WO | WO 03/013573 A1 | 2/2003 |
| WO | WO 03/030821 A2 | 4/2003 |
| WO | WO 03/059934 A2 | 7/2003 |
| WO | WO 03/059935 A2 | 7/2003 |
| WO | WO 03/059935 A3 | 7/2003 |
| WO | WO 03/060071 A2 | 7/2003 |
| WO | WO 03/068934 A2 | 8/2003 |
| WO | WO 03/068934 A3 | 8/2003 |
| WO | WO 03066824 A2 * | 8/2003 |
| WO | WO 03/076567 A2 | 9/2003 |
| WO | WO 03/087355 A1 | 10/2003 |
| WO | WO 03/093313 A2 | 11/2003 |
| WO | WO 2004/005347 A1 | 1/2004 |
| WO | WO 2004/021861 A2 | 3/2004 |
| WO | WO 2004/021861 A3 | 3/2004 |
| WO | WO 2004/081053 A1 | 9/2004 |
| WO | WO 2004/082640 A2 | 9/2004 |
| WO | WO 2004/101739 A2 | 11/2004 |
| WO | WO 2004/101739 A3 | 11/2004 |
| WO | WO 2004/101740 A2 | 11/2004 |
| WO | WO 2004/101740 A3 | 11/2004 |
| WO | WO 2005/000892 A2 | 1/2005 |
| WO | WO 2005/001025 A2 | 1/2005 |
| WO | WO 2005/001025 A3 | 1/2005 |
| WO | WO 2005/003296 A2 | 1/2005 |
| WO | WO 2005/024044 A2 | 3/2005 |
| WO | WO 2005/063808 A1 | 7/2005 |
| WO | WO 2005/077042 A2 | 8/2005 |
| WO | WO 2005/111074 A1 | 11/2005 |
| WO | WO 2005/111225 A1 | 11/2005 |
| WO | WO 2006/000448 A2 | 1/2006 |
| WO | WO 2006/018204 A1 | 2/2006 |
| WO | WO 2006/027111 A1 | 3/2006 |
| WO | WO 2006/108590 A1 | 10/2006 |
| WO | WO 2007/021494 A2 | 2/2007 |
| WO | WO 2007/115724 A2 | 10/2007 |
| WO | WO 2007/146038 A2 | 12/2007 |
| WO | WO 2008/098720 A1 | 8/2008 |

OTHER PUBLICATIONS

Office Action for co-pending U.S. Appl. No. 11/812,016, mailed Dec. 7, 2009.

Kurachi, K., et al., "Isolation and characterization of a cDNA coding for human factor IX," PNAS 79: 6461-6464 (1982).

(56) References Cited

OTHER PUBLICATIONS

European Search Report; dated Jan. 24, 2007, for App. No. 06012262.9-2403.
Patent Cooperation Treaty International Search Report; dated Sep. 28, 2007, for App. No. PCT/EP2007/005246.
Aledort, L.M., Comparative Thrombotic Event Incidence After Infusion of Recombinant Factor VIIa Versus Factor VIII Inhibitor Bypass Activity, *J. Thromb. Haemost.*, 2: 1700-1708 (2004).
Beattie, W.G. and Dugaiczyk A., Structure and Evolution of Human α-Fetoprotein Deduced From Partial Sequence of Cloned cDNA; *Gene*, 20: 415-422 (1982).
Chaudhury, C., et al., The Major Histocompatibility Complex-related Fc Receptor for IgG (FcRn) Binds Albumin and Prolongs Its Lifespan, *J. Exp. Med.*, 197(3): 315-322 (2003).
Cooke, N.E. and David, E. V., Serum Vitamin D-binding Protein is a Third Member of the Albumin and Alpha Fetoprotein Gene Family, *J. Clin. Invest.*, 76: 2420-2424 (1985).
DiScipio, R.G., et al., A Comparison of Human Prothrombin, Factor IX (Christmas Factor), Factor X (Stuart Factor), and Protein S, *Biochemistry*, 16(4): 698-706 (1977).
Ewenstein, B.M., et al., Pharmacokinetic Analysis of Plasma-Derived and Recombinant F IX Concentrates in Previously Treated Patients With Moderate or Severe Hemophilia B, *Transfusion*, 42: 190-197 (2002).
Lichenstein, H.S., et al., Afamin Is a New Member of the Albumin, α-Fetoprotein, and Vitamin D-binding Protein Gene Family, *J. Biol. Chem.*, 269(27): 18149-18154 (1994).
Wasley, L.C., et al., PACE/Furin Can Process the Vitamin K-dependent Pro-factor IX Precursor Within the Secretory Pathway, *J. Biol. Chem.*, 268(12): 8458-65 (1993).
White, G.C., et al., Recombinant Factor IX, *Thrombosis and Haemostasis*, 78(1): 261-265 (1997).
Erhardtsen; "To General Haemostasis—The Evidence-Based Route", Pathophysiol Haemost Thromb, vol. 23(suppl. 1), pp. 47-52, (2002).
Mollerup et al.; "The Use of RP-HPLC for Measuring Activation and Cleavage of rFVIIa During Purification", Biotechnology and Bioengineering, vol. 48, pp. 501-505, (1995).
Sheffield et al.; "Effects of Genetic Fusion of Factor IX to Albumin on In Vivo Clearance in Mice and Rabbits", British Journal of Haematology, vol. 126, pp. 565-573, (2004).
Lindley et al.; "Pharmacokinetics and Pharmacodynamics of Recombinant Factor VIIa", Clinical Pharmacology & Therapeutics, vol. 55, No. 6, pp. 638-648, (1994).
O'Reilly et al.; "Antiangiogenic Activity of the Cleaved Conformation of the Serpin Antithrombin", Science vol. 285, pp. 1926-1928, (1999).
Shah et al.; "Manipulation of the Membrane Binding Site of Vitamin K-Dependent Proteins: Enhanced Biological Function of Human Factor VII", Proc. Natl. Acad. Sci. USA, Biochemistry, vol. 95, pp. 4229-4234, (1998).
Seligsohn et al.; "Coupled Amidolytic Assay for Factor VII: Its Use With a Clotting Assay to Determine the Activity State of Factor VII", The American Society of Hematology, Blood, vol. 52, No. 5, pp. 978-988, (1978).
Morrissey et al.; "Quantitation of Activated Factor VII Levels in Plasma Using a Tissue Factor Mutant Selectively Deficient in Promoting Factor VII Activation", The American Society of Hematology, Blood, vol. 81, No. 3, pp. 734-744, (1993).
Syed et al.; "Potent Antithrombin Activity and Delayed Clearance From the Circulation Characterize Recombinant Hirudin Genetically Fused to Albumin", The American Society of Hematology, Blood, vol. 89, No. 9, pp. 3243-3252, (1997).
Prescott et al.; "The Length of Polypeptide Linker Affects the Stability of Green Fluorescent Protein Fusion Proteins", Analytical Biochemistry, vol. 273, pp. 305-307, (1999).
International Search Report dated Aug. 22, 2006, for European patent application No. 06002359.5, filed Feb. 6, 2006.

Lee, G., Book Review of "Pharmaceutical Formulation Development of Peptides and Proteins" by Sven Frokjaer et al., *European Journal of Pharmaceutics and Biopharmaceutics*, vol. 50, p. 329 (2000).
Bettini, R., et al., Book Review of "Handbook of Pharmaceutical Excipients," Third Edition, Arthur H. Kibbe (ed.), *Journal of Controlled Release*, vol. 71, pp. 352-353 (2001).
Office Actions mailed Jul. 20, 2010, and Oct. 25, 2010, in U.S. Appl. No. 11/812,016.
Office Actions mailed Jul. 21, 2010, and Dec. 30, 2010, in U.S. Appl. No. 12/000,739.
Bick R.L. et al., "Physiology of Hemostasis," Clin. Lab. Med., 14(4):677-707 (1994).
Chaudhury C. et al., "The Major Histocompatibility Complex-Related Fc Receptor for IgG (FcRn) Binds Albumin and Prolongs its Lifespan," J. Exp. Med., 179:315-22 (2003).
Colman R.W. et al., Excerpts from "Homeostasis and thrombosis: Basic Principles & Clinical Practice," $4^{th}$ ed., Philadelphia, Lippincott Williams & Wilkins, 2001, pp. 34-35, 40-41, 103-104, 128-129, 159, 176, and 194.
Colman R.W. et al., *Overview of Hemostasis*, in Hemostasis and Thrombosis $4_{th}$ Ed., Chapter 1 (Colman et al. eds., Lippincott Williams & Wilkis, 2001).
Doolittle R.F., "The Evolution of Vertebrate Blood Coagulation: A Case of Yin and Yang," Thrombosis and Haemostasis, 70:24-28 (1993).
Duttaroy A. et al., "Development of a Long-Acting Insulin Analog Using Albumin Fusion Technology," Diabetes, 54:251-58 (2005).
Greenberg D.L. et al., *Blood Coagulation Factors: Their Complementary DNAs, Genes, and Expression*, in Hemostasis and Thrombosis $4^{th}$ Ed., Chapter 3 (Colman et al. eds., Lippincott Williams & Wilkins, 2001).
Halpern W. et al., "Albugranin™, a Recombinant Human Granulocyte colony stimulating Factor (G-CSF) Genetically Fused to Recombinant Human Albumin Induces Prolonged Myelopoietic Effects in Mice and Monkeys," Pharmaceutical Research, 19:1720-29 (2002).
Hansson K. et al., "Post-Translational Modifications in Proteins Involved in Blood Coagulation," J. Thrombosis and Haemostasis, 3:2633-48 (2005).
Marques J.A. et al., "A Barbourin-Albumin Fusion Protein that is Slowly Cleared in vivo Retains the Ability to Inhibit Platelet Aggregation in vitro," Thromb Haemost, 86:902-08 (2001).
Melder R.J. et al., "Pharmacokinetics and in vitro and in vivo Anti-Tumor Response of an Interleukin-2-Human Serum Albumin Fusion Protein in Mice," Cancer Immunol Immunother, 54:535-47 (2005).
Osborn B.L. et al., "Pharmacokinetic and Pharmacodynamic Studies of a Human Serum Albumin-Interferon-α Fusion Protein in Cynomolgus Monkeys," J. Pharmacology and Experimental Therapeutics, 303:540-48 (2002).
Osborn B.L. et al., "Albutropin: A Growth Hormone-Albumin Fusion with Improved Pharmacokinetics and Pharmacodynamics in Rats and Monkeys," European J. Pharmacology, 456:149-58 (2002).
Persson E., "Structure of Human Coagulation Activated Factor VII," Blood Coagulation and Fibrinolysis, 11(supp. 1):S17-S17 (2000).
Sheffield W.P. et al., "Prolonged in vivo anticoagulant activity of a hirudin-albumin fusion protein secreted from Pichia pastoris," Blood Coagulation and Fibrinolysis, 12:433-43 (2001).
Stenflo J., "Contributions of Gla and EGF-Like Domains of the Function of Vitamin K-Dependent Coagulation Factors," Critical Reviews™ in Eukaryotic Gene Expression, 9:59-88 (1999).
Syed S. et al., "Potent Antithrombin Activity and Delayed Clearance From the Circulation Characterize Recombinant Hirudin Genetically Fused to Albumin," Blood, 99:3243-52 (1997).
Wang W. et al., "AlbuBNP, a Recombinant B-Type Natriuretic Peptide and Human Serum Albumin Fusion Hormone, as a Long-Term Therapy of Congestive Heart Failure," Pharmaceutical Research, 21:2105-11 (2004).
Wriggers W. et all., "Biopolymers," Peptide Science, 80:736-46 (2005).
Yao Z. et al., "Effect of Albumin Fusion on the Biodistribution of Interleukin-2," Cancer Immunol Immunother, 53:404-10 (2004).
European Search Report and Written Opinion for Application No. 10164043.1-1212 mailed Aug. 24, 2010.

(56) References Cited

OTHER PUBLICATIONS

Schulte, "Use of albumin fusion technology to prolong the half-life of recombinant factor VIIa," Thrombosis Research, 122(suppl. 4):S14-S19 (2008).
Weimer et al., "Prolonged in-vivo half-life of factor VIIa by fusion to albumin," Thromb Haemost, 99:659-67 (2008).
"Clinical Trials" *Biotechnology Law Report*, 20(4):555-570 (2001).
"Regulatory Affairs—Pharmaceutical" *Biotechnology Law Report*, 20(5):707-713 (2001) (abstract).
Amano, K. et al., "Mutation at either Arg336 or Arg562 in Factor VIII Is Insufficient for Complete Resistance to Activated Protein C (APC)-mediated Inactivation: Implications for the APC Resistance Test" *Thromb. Haemost.*, 79:557-563 (1998).
Ananyeva, N.M. et al., "Catabolism of the Coagulation Factor VIII: Can We Prolong Lifetime of fVIII in Circulation?" *Trends Cardiovasc. Med.*, 11(6):251-257 (2001).
Anonymous, "Use of Recombinant Human Albumin in the Formulation of Proteins" Research Disclosure / 516, Disclosed Anonymously, 37603 (Aug. 1995); Publisher: Kenneth Mason Publications Ltd, Hampshire PO10 7DQ, England.
Ballance, D.J., "Yeast-Derived Recombinant Human Albumin (Recombumin™)" *Anästhesiol. Intensivmed. Notfallmed. Schmerzther*. 34:775-777 (1999).
Belaaouaj et al., "Matrix Metalloproteinases Cleave Tissue Factor Pathway Inhibitor" *J. Biol. Chem.*, 275(35):27123-27128 (2000).
Bellon et al., "Chemical Structure of Two Fragments of Human Serum Albumin and their Location in the Albumin Molecule" *Biochem. J.*, 147:585-592 (1975).
Berrettini et al., "Pharmacokinetic Evaluation of Recombinant, Activated Factor VII in Patients with Inherited Factor VII Deficiency" *Haematologica*, 86(6):640-645 (2001).
Bick, R.L. et al., "Factor V: a Simplified One-Stage Assay using a Stabilized Artificial Substrate" *Beitr. Path. Bd.*, 150:311-315 (1973).
Brennan et al., "Albumin Redhill (-1 Arg, 320 Ala → Thr): A glycoprotein variant of human serum albumin whose precursor has an aberrant signal peptidase cleavage site" *Proc. Natl. Acad. Sci. USA*, 87:26-30 (1990).
Brinkhous et al., "Effect of Recombinant Factor VIIa on the Hemostatic Defect in Dogs with Hemophilia A, Hemophilia B, and von Willebrand Disease" *Proc. Natl. Acad. Sci. USA*, 86:1382-1386 (1989).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue" *J. Cell. Biol.*, 111:2129-2138 (1990).
Carson and Konigsberg, "Cadmium increases tissue factor (coagulation factor III) activity by facilitating its reassociation with lipids" *Science*, 208(4441):307-309 (1980). (abstract only).
Chavin, S.I. And Weidner, S.M., "Blood Clotting Factor IX: Loss of Activity After Cleavage of Sialic Acid Residues" *J. Biol. Chem.*, 259(6):3387-3390 (1984).
Collins, C.J. et al., "Molecular cloning of the human gene for von Willebrand factor and identification of the transcription initiation site" *Proc. Natl. Acad. Sci. USA*, 84:4393-4397 (Jul. 1987).
Comp et al., "Determination of Functional Levels of Protein C, an Antithrombotic Protein, Using Thrombin-Thrombomodulin Complex" *Blood*, 63(1):15-21 (1984).
Dockal et al., "Five recombinant fragments of human serum albumin—Tools for the characterization of the warfarin binding site" *Protein Science*, 9:1455-1465 (2000).
Dockal et al., "The Three Recombinant Domains of Human Serum Albumin" *J. Biol. Chem.*, 274:29303-29310 (1999).
Dumont, J.A. et al., "Monomeric Fc Fusions" *BioDrugs*, 20(3):151-160 (2006).
European Search Report and Opinion issued in Application No. 06026747.3-2406, dated May 9, 2007.
European Search Report and Opinion issued in Application No. 10168156.7-1212, dated Nov. 22, 2010.
European Search Report and Opinion issued in Application No. 10168453.8-2403, dated Oct. 7, 2010.
Fay, P.J. And Smudzin, T.M., "Characterization of the Interaction between the A2 Subunit and A1/A3-C1-C2 Dimer in Human Factor VIIIa" *J. Biol. Chem.*, 267(19):13246-13250 (Jul. 5, 1992).
Fay, P.J. et al., "Human Factor VIII$_a$ Subunit Structure. Reconstitution of Factor VIII, from the Isolated A1/A3-C1-C2 Dimer and A2 Subunit" *J. Biol. Chem.*, 266(14):8957-8962 (1991).
Federici, A.B. et al., "A sensitive ristocetin co-factor activity assay with recombinant glycoprotein Ibα for the diagnosis of patients with low von Willebrand factor levels" *haematologica*, 89(1):77-85 (2004).
Gale, A.J. And Pellequer, J.L., "An engineered interdomain disulfide bond stabilizes human blood coagulation factor VIIIa" *J. Thromb. Haemost.*, 1:1966-1971 (2003).
Gale, A.J. et al., "Interdomain engineered disulfide bond permitting elucidation of mechanisms of inactivation of coagulation factor Va by activated protein C" *Protein Science*, 11: 2091-2101 (2002).
Gale, A.J. et al., "Intrinsic stability and functional properties of disulfide bond-stabilized coagulation factor VIIIa variants" *J. Thromb. Haemost.*, 4:1315-1322 (2006).
Gales, B.J. And Erstad, B.L., "Adverse Reactions to Human Serum Albumin" *The Annals of Pharmacotherapy*, 27:87-94 (1993).
Galliano et al., "Mutations in genetic variants of human serum albumin found in Italy" *Proc. Natl. Acad. Sci. USA*, 87:8721-8725 (1990).
Geisow et al., "Physical and Binding Properties of Large Fragments of Human Serum Albumin" *Biochem. J.*, 163:477-484 (1977).
Guo et al., "Protein tolerance to random amino acid change" *PNAS*, 101(25):9205-9210 (2004).
Hagen et al., "Characterization of a cDNA coding for human factor VII" *Proc. Natl. Acad. Sci. USA*, 83: 2412-2416 (1986).
Heeb, M.J. et al., "Protein S multimers and monomers each have direct anticoagulant activity" *J. Thromb. Haemost.*, 4:385-391 (2006).
Higashi and Iwanaga, "Molecular interaction between factor VII and tissue factor" *Int. J. Hematol.*, 67(3): 229-241 (1998) (abstract only).
Hollon, T., "HGS Targets Patent-Expiring Drugs" *Nature Biotechnology*, 18(12):1238-1239 (2000).
Holt, L.J. et al., "Domain Antibodies: Proteins for Therapy" *Trends in Biotechnology*, 21(11):484-490 (2003).
International Search Report and Written Opinion issued in International Patent Application No. PCT/EP2007/000937; Date of Mailing: May 18, 2007.
International Search Report and Written Opinion issued in International Patent Application No. PCT/EP2007/002948; Date of Mailing: Jan. 24, 2008.
International Search Report and Written Opinion, issued in International Patent Application No. PCT/EP2007/011356; Date of Mailing: Mar. 26, 2008.
Kallas, A. and Talpsep, T., "The von Willebrand factor collagen-binding activity assay: clinical application" *Ann. Hematol.*, 80:466-471 (2001).
Kazama et al., "Evidence that an Arg79→Gln substitution in human factor VII is not associated with a reduction in coagulant activity" *Blood Coagul. Fibrinolysis*, 3(6):697-702 (1992) (abstract only).
Leonard et al., "Factor VII Deficiency Caused by a Structural Variant N57D of the First Epidermal Growth Factor Domain" *Blood*, 91:142-148 (1998).
Lin, Y. et al., "Use of blood outgrowth endothelial cells for gene therapy for hemophilia A" *Blood*, 99(2):457-462 (Jan. 15, 2002).
Lollar, P., "Characterization of Factor VIII B-Cell Inhibitory Epitopes" *Thromb. Haemost.*, 82(2):505-508 (1999).
Lusher, J.M., et al., "In Vivo Recovery with Products of Very High Purity-Assay Discrepancies" *Haemophilia*, 4(4):641-645 (1998).
Madison et al., "Genetic variants of human serum albumin in Italy: Point mutants and a carboxyl-terminal variant" *Proc. Natl. Acad. Sci. USA*, 91:6476-6480 (1994).
Miao, H.Z. et al., "Bioengineering of coagulation factor VIII for improved secretion" *Blood*, 103(9):3412-3419 (May 1, 2004).
Mikaelsson, M. et al., "Potency and In Vivo Recovery of High Purity Factor VIII Concentrates" *Thromb. Haemost.*, 72(1):160-161 (1994).

(56) References Cited

OTHER PUBLICATIONS

Minchiotti et al., "The Molecular Defect in a COOH-terminal-modified and Shortened Mutant of Human Serum Albumin" *J. Biol. Chem.*, 264:3385-3389 (1989).

Nakayama, "Furin: a mammalian subtilisin/Kex2p-like endoprotease involved in processing of a wide variety of precursor proteins" *Biochem. J.*, 327:625-635 (1997).

Oh, S-H. et al., "Synthesis of recombinant blood coagulation factor VIII (FVIII) heavy and light chains and reconstitution of active form of FVIII" *Exp. Mol. Med.*, 31(2):95-100 (1999).

Peach et al., "Albumin Rugby Park: a truncated albumin variant caused by a G→C splice-site mutation in intron 13" *Biochim. Biophys. Acta*, 1180:107-110 (1992).

Petrovan, R.J. et al., "A Novel Clotting Assay for Quantitation of Plasma Prothrombin (Factor II) Using *Echis multisquamatus* Venom" *Am. J. Clin. Pathol.*, 112:705-711 (1999).

Pipe, S.W. And Kaufman, R.J., "Characterization of a genetically engineered inactivation-resistant coagulation factor VIIIa" *Proc. Natl. Acad. Sci. USA*, 94:11851-11856 (1997).

Pipe, S.W., "Coagulation Factors with Improved Properties for Hemophilia Gene Therapy" *Semin. Thromb. Hemost.*, 30(2):227-237 (2004).

Pittman, D.D. et al., "Biochemical, Immunological, and In Vivo Functional Characterization of B-Domain-Deleted Factor VIII" *Blood*, 81(11):2925-2935 (1993).

Poon, M-C. et al., "Recombinant Factor IX Recovery and Inhibitor Safety: A Canadian Post-licensure Surveillance Study" *Thromb. Haemost.* 87:431-435 (2002).

PR Newswire, "Human Genome Sciences Provides Update off Company Progress—Clinical Studies of a Human Monoclonal Antibody to TRAIL Receptor-1 Cleared by the U.S. Food an Drug Administration" [online]. Apr. 30, 2002. Retrieved from the Internet: http://www.prnewswire.com/news-releases/human-genome-sciences-provides-update-of-company-progress-77195997.html.

Rian, E. et al., "Synthesis of human parathyroid-hormone-related protein (1-141) in *Saccharomyces cerevisiae*: A correct amino-terminal processing vital for the hormone's biological activity is obtained by an ubiquitin fusion protein approach" *Eur. J. Biochem.*, 213(1):641-647 (1993).

Rizza, C.R. And Rhymes, I.L., "Coagulation Assay of VIIIC and IXC" In: *The Hemophilias. Methods in Hematology Series*, vol. 5. A. L. Bloom (ed.) New York: Churchill Livingstone, 1982; Chapter 2, pp. 18-38.

Rosén, S. "Assay of Factor VIII:C with a Chromogenic Substrate" *Scand. J. Haematol.* 33(Suppl. 40):139-145 (1984).

Röstin et al., "B-Domain Deleted Recombinant Coagulation Factor VIII Modified with Monomethoxy Polyethylene Glycol" *Bioconj. J.*, 11:387-396 (2000).

Ruf, W., "The interaction of activated factor VII with tissue factor: insight into the mechanism of cofactor-mediated activation of activated factor VII" *Blood Coagul. Fibrinolysis*, 9(Suppl 1): S73-S78 (1998) (abstract only).

Saenko, E.L. et al., "Molecular defects in coagulation Factor VIII and their impact on Factor VIII function" *Vox Sanguinis*, 83:89-96 (2002).

Sandberg, H. et al., "Structural and Functional Characteristics of the B-domain-deleted Recombinant Factor VIII Protein, r-VIII SQ" *Thromb. Haemost.*, 85:93-100 (2001).

Sheffield et al., "Effects of genetic fusion of factor IX to albumin on in vivo clearance in mice and rabbits" *Br. J. Hematol.* 126(4):565-573 (2004).

Subramanian, G.M. et al., "Albinterferon α-2b: A Genetic Fusion Protein for the Treatment of Chronic Hepatitis C" *Nature Biotechnology*, 25(12):1411-1419 (2007).

Sucker, C. et al., "Determination of von Willebrand Factor Activity: Evaluation of the HaemosIL™ Assay in Comparison with Established Procedures" *Clin. Appl. Thromb./Hemost.*, 12(3):305-310 (2006).

Sugio et al., "Crystal structure of human serum albumin at 2.5 Å resolution" *Protein Engineering*, 12:439-446 (1999).

Sung, C., et al., "An IFN-Beta-Albumin Fusion Protein That Displays Improved Pharmacokinetic and Pharmacodynamic Properties in Nonhuman Primates" *Journal of Interferon and Cytokine Research*, 23(1):25-36 (2003).

Swaroop, M. et al., "Mutagenesis of a Potential Immunoglobulin-binding Protein-binding Site Enhances Secretion of Coagulation Factor VIII" *J. Biol. Chem.*, 272(39):24121-24124 (1997).

Tabatabai, A. et al., "Protein Z Circulates in Plasma in a Complex with Protein Z-Dependent Protease Inhibitor" *Thromb. Haemost.*, 85:655-660 (2001).

Takahashi et al., "Structural changes and metal binding by proalbumins and other amino-terminal genetic variants of human serum albumin" *Proc. Natl. Acad. Sci. USA*, 84:7403-7407 (1987).

Traub, A. et al., "Interferon-Albumin Conjugate with Conserved Biological Activity" *J. Gen. Virol.*, 53(2):389-392 (1981).

U.S. Appl. No. 11/927,583 by Ballance et al., filed Oct. 29, 2007.

U.S. Appl. No. 11/927,583: Restriction Requirement, mailed Sep. 8, 2011.

U.S. Appl. No. 11/927,583: Non-Final Office Action, mailed Dec. 5, 2011.

U.S. Appl. No. 11/927,593: Restriction Requirement, mailed May 6, 2009.

U.S. Appl. No. 11/927,593: Non-Final Office Action, mailed Jul. 9, 2009.

U.S. Appl. No. 11/927,593: Non-Final Office Action, mailed Sep. 17, 2010.

U.S. Appl. No. 11/927,593: Final Office Action, mailed Apr. 27, 2011.

U.S. Appl. No. 11/927,600 by Ballance et al., filed Oct. 29, 2007.

U.S. Appl. No. 11/927,600: Restriction Requirement, mailed Aug. 9, 2011.

U.S. Appl. No. 11/927,600: Non-Final Office Action, mailed Nov. 28, 2011.

U.S. Appl. No. 11/927,602: Restriction Requirement, mailed May 6, 2009.

U.S. Appl. No. 11/927,602: Non-Final Office Action, mailed Aug. 24, 2009.

U.S. Appl. No. 11/927,602: Non-Final Office Action, mailed Sep. 7, 2010.

U.S. Appl. No. 11/927,602: Final Office Action, mailed Apr. 28, 2011.

U.S. Appl. No. 11/927,607: Restriction Requirement, mailed May 6, 2009.

U.S. Appl. No. 11/927,607: Non-Final Office Action, mailed Aug. 25, 2009.

U.S. Appl. No. 11/927,607: Final Office Action, mailed Mar. 31, 2010.

U.S. Appl. No. 11/927,607: Non-Final Office Action, mailed Sep. 20, 2010.

U.S. Appl. No. 11/927,607: Non-Final Office Action, mailed Jun. 21, 2011.

U.S. Appl. No. 11/927,610: Restriction Requirement, mailed May 5, 2009.

U.S. Appl. No. 11/927,610: Non-Final Office Action, mailed Aug. 25, 2009.

U.S. Appl. No. 11/927,610: Final Office Action, mailed Apr. 1, 2010.

U.S. Appl. No. 11/927,610: Non-Final Office Action, mailed Sep. 20, 2010.

U.S. Appl. No. 11/927,610: Final Office Action, mailed Apr. 11, 2011.

U.S. Appl. No. 11/929,702: Restriction Requirement, mailed Sep. 9, 2009.

U.S. Appl. No. 11/929,702: Non-Final Office Action, mailed Dec. 29, 2009.

U.S. Appl. No. 11/812,016: Restriction Requirement, mailed Jul. 15, 2009.

U.S. Appl. No. 12/000,739: Restriction Requirement, mailed Mar. 31, 2010.

U.S. Appl. No. 12/226,188: Final Office Action, mailed Dec. 21, 2011.

U.S. Appl. No. 12/226,188: Non-Final Office Action, mailed May 12, 2011.

(56) References Cited

OTHER PUBLICATIONS

U.S. Appl. No. 12/520,840: Non-Final Office Action, mailed Dec. 7, 2011.
U.S. Appl. No. 12/520,840: Restriction Requirement, mailed Oct. 13, 2011.
U.S. Appl. No. 13/074,153: Non-Final Office Action, mailed Feb. 23, 2012.
U.S. Appl. No. 13/212,879 by Ballance et al., filed Aug. 18, 2011.
Van Wijk, E.M. et al., "A Rapid Manual Chromogenic Factor X Assay" *Thromb. Res.*, 22:681-686 (1981).
Vehar, G.A. et al., "Structure of human factor VIII" *Nature*, 312:337-342 (1984).
Wakabayashi, H. et al., "A Glu113Ala Mutation within a Factor VIII $Ca^{2+}$-Binding Site Enhances Cofactor Interactions in Factor Xase" *Biochem.*, 44:10298-10304 (2005).
Watkins et al., "cDNA and protein sequence of polymorphic macaque albumins that differ in bilirubin binding" *Proc. Natl. Acad. Sci. USA*, 90:2409-2413 (1993).
White et al., "Clinical Evaluation of Recombinant Factor IX", *Seminars in Hematology*, 35(2, Suppl 2):33-38 (1998).
Wood, W.I. et al., "Expression of active human factor VIII from recombinant DNA clones" *Nature*, 312:330-337 (1984).
Yeh et al., "Design of yeast-secreted albumin derivatives for human therapy: biological and antiviral properties of a serum albunin-CD4 genetic conjugate", *Proc. Natl. Acad. Sci. USA*, 89(5):1904-1908 (1992).
Zollner, S. et al., "Prolonged serum half-life of a recombinant, albumfused, human coagulation factor IX(rIX-FP) in different animal species" Poster from the 2010 Hemophilia World Congress sponsored by the World Federation of Hemophilia, in Buenos Aires, Argentina, Jul. 10-Jul. 14, 2010.
"A Safety and Pharmacokinetics Study of a Recombinant Fusion Protein Linking Coagulation Factor VIIa With Albumin (rVIIa-FP) in Healthy Male Volunteers," Mar. 7, 2013 [online]. Downloaded from http://clinicaltrials.gov/ct2/show/NCT01542619?term=CSL689_1001&rank=1 on Oct. 28, 2013.
Australian Office Action for Australian Patent Application No. 2007338298, dated Nov. 23, 2011.
Bayer News Release, "Bayer Provides Update on Phase II/III Trial of BAY 86/6150," 2013.
Bonthron et al., "Nucleotide sequence of pre-pro-von Willebrand factor cDNA," *Nucleic Acids Res.* 14: 7125-7127 (1986).
Butenas et al., "Synthetic Substrates for Human Factor VIIa and Factor VIIa-Tissue Factor," *Biochemistry*, 32:6531-6538 (1993).
"Condensed Table of FVIII Point Mutations," Nov. 30, 2012 [online]. Downloaded from http://hadb.org.uk/WebPges/PublicFiles/CondensedPoints.htm on Feb. 11, 2013.
European Application No. 01934875: Supplementary Partial European Search Report, completed Jun. 4, 2003 (5 pages).
European Application No. 10075391.2: Extended Search Report, dated Jan. 28, 2011 (4 pages).
European Application No. 10075010: Search Report, dated May 20, 2010 (2 pages).
Fijnvandraat et al., "Recombinant, B-domain Deleted Factor VIII (r-VIII SQ): Pharmacokinetics and Initial Safety Aspects in Hemophilia A Patients" *Thrombosis and Haemostasis*, 77(2):298-302 (1997).
Golor et al., "Safety and Pharmacokinetics of a Recombinant Fusion Protein Linking Coagulation Factor Iia with Albumin (rVIIa-FP) in Healthy Volunteers," *Clinical Haemostasis and Thrombosis*, accepted article (2013).
Hoots et al., "Continuous intravenous infusion of a plasma-derived factor IX concentrate (Mononine®) in haemophilia B" *Haemophilia*, 9(2):164-172 (Mar. 2003).
International Preliminary Examination Report issued in International Patent Application No. PCT/US01/12009; Date of Completion: Mar. 13, 2003 (7 pages).
International Search Report issued in International Patent Application No. PCT/US02/40891; Date of Mailing: Apr. 21, 2003.
Japanese Office Action for Japanese Patent Application No. 2008-552755, dated Jun. 19, 2012, with English translation (9 pages).
Japanese Office Action for Japanese Patent Application No. 2009-504607, dated Jun. 26, 2012, with English translation (13 pages).
Japanese Office Action for Japanese Application No. 2009-514703 dated, Jul. 3, 2012, with English translation (16 pages).
Japanese Office Action for Japanese Application No. 2009-541911, dated Jul. 3, 2012, with English translation (6 pages).
Japanese Office Action for Japanese Application No. 2009-541911, dated Apr. 2, 2013, with English translation.
Ljung et al., "40K glycoPEGylated, recombinant FVIIa: 3-month, double-blind, randomized trial of safety, pharmacokinetics and preliminary efficacy in hemophilia patients with inhibitors," *Journal of Thrombosis and Haemostasis*, 11: 1260-1268 (2013).
Mahlangu et al., "Phase I, randomized, double-blind, placebo-controlled, single-dose escalation study of the recombinant factor VIIa variant BAY 86-6150 in hemophilia," *Journal of Thrombosis and Haemostasis*, 10: 773-780 (2012).
Novo Nordisk Company Announcement, "Interim financial report from the period Jan. 1, 2011 to Sep. 30, 2011," Oct. 27, 2011.
Pipe, S.W., "Functional Roles of the Factor VIII B Domain," *Haemophilia*, 15:1187-1196 (2009).
Roth et al., "Human recombinant factor IX: safety and efficacy studies in hemophilia B patients previously treated with plasma-derived factor IX concentrates," *Blood*, 98:3600-3606 (2001).
Ruggeri, Z.M., "Structure and function of von Willebrand factor," *Thromb. Haemost.* 82: 576-584 (1999).
Santagostino et al., "Safety and pharmacokinetics of a novel recombinant fusion protein linking coagulation factor IX with albumin (rIX-FP) in hemophilia B patients," *Blood*, 120(12):2405-2011 (2012).
Shapiro et al., "The safety and efficacy of recombinant human blood coagulation factor IX in previously untreated patients with severe or moderately severe hemophilia B", published online before print, Sep. 21, 2004; final publication in vol. 105, No. 2, pp. 518-525 (Jan. 15, 2005).
Stanssens et al., "Anticoagulant repertoire of the hookworm *Ancylostoma caninum*," *Proc. Natl. Acad. Sci. USA*, 93:2149-2154 (1996).
Tanaka et al., "Blood Coagulation: Hemostasis and Thrombin Regulation," *Anesth. Analg.* 108:1433-1446 (2009).
U.S. Appl. No. 11/597,593: Non-Final Office Action, mailed Jul. 9, 2009.
U.S. Appl. No. 11/597,593: Non-Final Office Action, mailed Sep. 17, 2010.
U.S. Appl. No. 11/597,593: Final Office Action, mailed Apr. 27, 2011.
U.S. Appl. No. 11/927,593: Non-Final Office Action, mailed Jun. 4, 2013.
U.S. Appl. No. 11/927,600: Non-Final Office Action, mailed Jun. 6, 2012.
U.S. Appl. No. 11/927,600: Final Office Action, mailed Jul. 18, 2012.
U.S. Appl. No. 11/927,602: Non-Final Office Action, mailed May 23, 2013.
U.S. Appl. No. 12/226,188: Final Office Action, mailed May 15, 2012.
U.S. Appl. No. 12/226,188: Final Office Action, mailed Nov. 9, 2012.
U.S. Appl. No. 12/226,188: Final Office Action, mailed Mar. 29, 2013.
U.S. Appl. No. 12/520,840: Non-Final Office Action, mailed Jun. 5, 2012.
U.S. Appl. No. 12/520,840: Final Office Action, mailed Nov. 2, 2012.
U.S. Appl. No. 12/520,840: Non-Final Office Action, mailed Jun. 28, 2013.
U.S. Appl. No. 13/074,153: Final Office Action, mailed Jul. 18, 2012.
U.S. Appl. No. 13/212,879: Restriction Requirement, mailed Aug. 14, 2012.
U.S. Appl. No. 13/212,879: Non-Final Office Action, mailed Nov. 8, 2012.
U.S. Appl. No. 13/212,879: Final Office Action, mailed Oct. 22, 2013.
U.S. Appl. No. 13/921,815: Non-Final Office Action, mailed Oct. 2, 2013.

\* cited by examiner

Figure 1:

```
                      XhoI                                              NotI
..CTGCGAGCCCCATTTCCCTCGAGGGCCGCCGCAAGGGCGAATTCGGATCCGCGGCCGCA
..  L   R   A   P   F   P
```

Figure 2:

| | Factor VII | | albumin |
|---|---|---|---|
| pFVII-974 | ...LRAPFP | | DAHKSE... |
| pFVII-1158 | ...LRAPFP | G | DAHKSE... |
| pFVII-1159 | ...LRAPFP | GS | DAHKSE... |
| pFVII-1160 | ...LRAPFP | GGS | DAHKSE... |
| pFVII-1370 | ...LRAPFP | SSGS | DAHKSE... |
| pFVII-1361 | ...LRAPFP | SS GGS | DAHKSE... |
| pFVII-1362 | ...LRAPFP | S GGS GS | DAHKSE... |
| pFVII-1363 | ...LRAPFP | SS GGS GS | DAHKSE... |
| pFVII-1382 | ...LRAPFP | SS (GGS)$_4$ GS | DAHKSE... |
| pFVII-935 | ...LRAPFP | SS (GGS)$_5$ GS | DAHKSE... |
| pFVII-936 | ...LRAPFP | SS (GGS)$_7$ GS | DAHKSE... |
| pFVII-937 | ...LRAPFP | SS (GGS)$_9$ GS | DAHKSE... |
| pFVII-1016 | ...LRAPFP | SS NGS GS | DAHKSE... |
| pFVII-1015 | ...LRAPFP | SS NGS GGS GS | DAHKSE... |
| pFVII-1014 | ...LRAPFP | SS NGS GGS GGN GS | DAHKSE... |
| pFVII-938 | ...LRAPFP | SS NGS (GGS)$_3$ GGN GS | DAHKSE... |
| pFVII-939 | ...LRAPFP | SS NGS (GGS)$_5$ GGN GS | DAHKSE... |
| pFVII-940 | ...LRAPFP | SS NGS (GGS)$_7$ GGN GS | DAHKSE... |
| pFVII-941 | ...LRAPFP | SS NGS (GGS)$_3$ NGS (GGS)$_3$ GGN GS | DAHKSE... |
| pFVII-834 | ...LRAPFP | SS VPRAV GGS (GGS)$_2$ GS | DAHKSE... |

MODIFIED COAGULATION FACTOR VIIA WITH EXTENDED HALF-LIFE

CROSS REFERENCE TO RELATED APPLICATIONS

This application is a national stage filing under 35 U.S.C. §371 of International Application No. PCT/EP2007/000937, filed on Feb. 3, 2007, which claims the benefit of priority of European Application No. EP06002359.5, filed on Feb. 6, 2006. Both of these applications are incorporated herein by reference in their entirety.

FIELD OF THE INVENTION

The present invention relates to the fields of Factor VII (FVII) and Factor VIIa (FVIIa) albumin linked polypeptides. More specifically, the invention relates to cDNA sequences coding for human Factor VII and Factor VIIa and derivatives genetically fused to a cDNA coding for human serum albumin which may be linked by oligonucleotides which code for intervening peptidic linkers such encoded derivatives exhibiting improved stability and extended functional plasma half-life, recombinant expression vectors containing such cDNA sequences, host cells transformed with such recombinant expression vectors, recombinant polypeptides and derivatives which do have biological activities of the unmodified wild type protein but having improved stability and prolonged shelf-life and processes for the manufacture of such recombinant proteins and their derivatives. The invention also covers a transfer vector for use in human gene therapy, which comprises such modified DNA sequences.

BACKGROUND OF THE INVENTION

Factor VII and Factor VIIa

Hemophilia A is an inherited bleeding disorder. It results from a chromosome X-linked deficiency of blood coagulation Factor VIII, and affects almost exclusively males with an incidence between one and two individuals per 10,000. The X-chromosome defect is transmitted by female carriers who are not themselves hemophiliacs. The clinical manifestation of hemophilia A is an increased bleeding tendency. Before treatment with Factor VIII concentrates was introduced the mean life span for a person with severe hemophilia was less than 20 years. The use of concentrates of Factor VIII from plasma and later on of recombinant forms of Factor VIII has considerably improved the situation for the hemophilia patients increasing the mean life span extensively, giving most of them the possibility to live a more or less normal life. Hemophilia B being 5 times less prevalent than hemophilia A is caused by non-functional or missing Factor IX and is treated with Factor IX concentrates from plasma or a recombinant form of Factor IX. In both hemophilia A and in hemophilia B the most serious medical problem in treating the disease is the generation of alloantibodies against the replacement factors. Up to 30% of all hemophilia A patients develop antibodies to Factor VIII. Antibodies to Factor IX occur to a lesser extent but with more severe consequences, as they are less susceptible to immune tolerance induction therapy.

The current model of coagulation states that the physiological trigger of coagulation is the formation of a complex between tissue Factor (TF) and Factor VIIa (FVIIa) on the surface of TF expressing cells, which are normally located outside the vasculature. This leads to the activation of Factor IX and Factor X ultimately generating some thrombin. In a positive feedback loop thrombin activates Factor VIII and Factor IX, the so-called "intrinsic" arm of the blood coagulation cascade, thus amplifying the generation of Factor Xa, which is necessary for the generation of the full thrombin burst to achieve complete hemostasis. It was shown that by administering supraphysiological concentrations of Factor VIIa hemostasis is achieved bypassing the need for Factor VIIIa and Factor IXa. The cloning of the cDNA for Factor VII (U.S. Pat. No. 4,784,950) made it possible to develop activated Factor VII as a pharmaceutical. Factor VIIa was successfully administered for the first time in 1988. Ever since the number of indications of Factor VIIa has grown steadily showing a potential to become a universal hemostatic agent to stop bleeding (Erhardtsen, 2002). However, the short half-life of Factor VIIa of approximately 2 hours is limiting its application.

FVII is a single-chain glycoprotein with a molecular weight of about 50 kDa, which is secreted by liver cells into the blood stream as an inactive zymogen of 406 amino acids. It contains 10γ-carboxy-glutamic acid residues (positions 6, 7, 14, 16, 19, 20, 25, 26, 29, and 35) localized in the N-terminal Gla-domain of the protein. The Gla residues require vitamin K for their biosynthesis. Located C-terminal to the Gla domain are two epidermal growth factor domains followed by a trypsin-type serine protease domain. Further post-translational modifications of FVII encompass hydroxylation (Asp 63), N-(Asn145 and Asn322) as well as O-type glycosylation (Ser52 and Ser60).

FVII is converted to its active form Factor VIIa by proteolysis of the single peptide bond at Arg152-Ile153 leading to the formation of two polypeptide chains, a N-terminal light chain (24 kDa) and a C-terminal heavy chain (28 kDa), which are held together by one disulfide bridge. In contrast to other vitamin K-dependent coagulation factors no activation peptide, which is cleaved off during activation of these other vitamin-K dependent coagulation factors has been described for FVII. The Arg152-Ile153 cleavage site and some amino acids downstream show homology to the activation cleavage site of other vitamin K-dependent polypeptides.

Essential for attaining the active conformation of Factor VIIa is the formation of a salt bridge after activation cleavage between Ile153 and Asp343. Activation cleavage of Factor VII can be achieved in vitro by Factor Xa, Factor XIIa, Factor IXa, Factor VIIa, Factor Seven Activating Protease (FSAP) and thrombin. Mollerup et al. (Biotechnol. Bioeng. (1995) 48: 501-505) reported that some cleavage also occurs in the heavy chain at Arg290 and or Arg315.

Factor VII is present in plasma in a concentration of 500 ng/ml. 1%, e.g. 5 ng/ml of Factor VII is present as Factor VIIa. Plasma half-life of Factor VII was found to be about 4 hours and that of Factor VIIa about 2 hours. Although the half-life of Factor VIIa of 2 hours is comparatively long for an activated coagulation factor (which is, for other activated coagulation factors more in the order of minutes due to the irreversible inhibition by serpins like antithrombin III) this nevertheless constitutes a severe drawback for the therapeutic use of Factor VIIa, as it leads to the need of multiple i.v. injections or continuous infusion to achieve hemostasis. This results in very high cost of treatment and inconvenience for the patient. Up to now no pharmaceutical preparation of a Factor VIIa with improved plasma half-life is commercially available nor have any data been published showing FVII/FVIIa variants with prolonged in vivo half-life. As Factor VII/VIIa has the potential to be used as a universal hemostatic agent a high medical need still exists to develop forms of Factor VIIa which have a longer functional half-life in vivo.

Ballance et al. (WO 01/79271) describes fusion polypeptides of a multitude of different therapeutic proteins or variants and/or fragments of said therapeutic proteins which, when fused to human serum albumin, or variants and/or fragments of said albumin are predicted to have increased functional half-life in vivo and extended shelf-life. Long lists of potential fusion partners are described without showing by experimental data for almost all of these proteins that the respective albumin fusion polypeptides actually retain biological activity of the therapeutic protein fusion partner and have improved properties. According to WO 01/79271 in addition each member from the list of therapeutic proteins can be fused in many different orientations to albumin e.g. two molecules of the therapeutic protein fused one to the N- and one to the C-terminus of albumin, or one molecule of the therapeutic protein fused either N-terminal or C-terminal to albumin, or also multiple regions of each protein fused to multiple regions of the other. Among the multitude of therapeutic proteins listed in WO 01/79271 as potential albumin fusion partners are Factor IX and FVII/FVIIa whereas no experimental proof of principle is provided for both proteins.

Sheffield expressed a Factor IX (a prothrombin factor consisting of 415 amino acids) albumin fusion polypeptide and showed in pharmacokinetic experiments that the clearance behaviour of the Factor IX albumin fusion polypeptide in rabbits resembled more closely that of Factor IX than that of albumin showing only a modest increase in terminal half-life (less than twofold) (Sheffield W P et al. (2004) Br. J. Haematol. 126:565-573).

In view of Sheffield's results and due to the high homology between Factors IX and VII (both are vitamin K dependent prothrombin factors) and their comparable size one skilled in the art would have assumed that also Factor VII will not profit from being fused to albumin in terms of functional half-life in vivo.

The technical problem underlying the present invention was therefore to develop functional FVIIa-albumin fusion proteins, which retain biological activity and show increased functional half-life in vivo.

In this respect, biological activity of a Factor VII/VIIa polypeptide refers to its ability to activate coagulation Factors IX and X in the presence of tissue factor after having been activated itself.

Functional plasma half-life in vivo refers to the half-life of the biological activity of the Factor VII/VIIa fusion polypeptide once injected into plasma. Preferably plasma is human plasma.

We find that albumin linked polypeptides comprising at least one Factor VII or Factor VIIa polypeptide or a fragment or variant thereof, fused to albumin, or a fragment or variant thereof wherein at least one Factor VII or Factor VIIa molecule is located at the N-terminus of the fusion protein, are resulting in fusion polypeptides with a biologically active Factor VII/Factor FVIIa moiety.

One aspect of the invention are therefore biologically active fusion proteins in which Factor VII/VIIa polypeptides are fused to the N-terminus of human serum albumin. The fusion proteins display at least 25%, preferably more than 40%, even more preferably more than 70% and most preferably more than 90% of the molar specific activity of wild-type Factor VII/VIIa.

It was further surprisingly found that in contrast to fusions of Factor IX to the N-terminus of human serum albumin as published by Sheffield, albumin fusions of Factor VII/VIIa to the N-terminus of human serum albumin led to Factor VII/FVIIa fusion proteins, which not only retained Factor VII/FVIIa biological activity but also displayed a significant extension of the functional plasma half-life of Factor VII/VIIa in vivo.

Expression of albumin fusion constructs with a desired FVII/FVIIa moiety at the C-terminus of albumin was not successful, because the expressed albumin fusion proteins were not secreted as intact molecules. Upon transition through the cell membrane a cleavage was observed into a mature FVII/FVIIa molecule, which due to impaired gamma-carboxylation had a reduced molar specific activity, and an albumin moiety with the FVII propeptide attached to its C-terminus. Thus it was found in contrast to the disclosure of Ballance et al., that only a fusion of the FVII/FVIIa moiety to the N-terminus of human serum albumin results in a fusion protein with the desired biological properties, respectively the retention of the biological activity of FVII/FVIIa and an increased plasma half-life.

A further aspect of the invention are therefore biologically active fusion proteins in which Factor VII/VIIa polypeptides are fused to the N-terminus of albumin which display a significant extension of the functional plasma half-life as compared to unfused Factor VII/VIIa. In preferred embodiments, FVII/FVIIa albumin fusion polypeptides of the invention comprising a FVII/FVIIa polypeptide have extended in vivo functional half-life or longer lasting or increased therapeutic activity compared to the in vivo half-life or therapeutic activity of unfused FVII/FVIIa.

One aspect of the invention are therefore FVII/FVIIa fused to the N-terminus of albumin extending the plasma half-life as compared to that of unfused FVII/FVIIa by at least 100%, preferably more than 200%, even more preferably more than 500%, most preferably more than 1000%.

In a further surprising aspect of the present invention we found that FVII/FVIIa albumin fusion polypeptides without a linker show significantly reduced biological activity, whereas FVII/FVIIa albumin fusion polypeptides in which the FVII/FVIIa moieties are separated from albumin by a linker exhibit linker-length dependent increase in Factor VII/VIIa biological activity. The Factor VII or Factor VIIa peptide portion is coupled to the albumin portion by a peptidic linker thus allowing the fusion molecule to assume a conformation, which allows for a higher molar specific activity compared to a fusion molecule without such linker sequence.

Therefore a further aspect of the invention are Factor VII/VIIa albumin fusion polypeptides comprising a linker peptide between the Factor VII/VIIa moiety and the N-terminus of albumin which have enhanced biological Factor VII/VIIa activity, e.g. measured as molar specific activity as compared to Factor VII/VIIa fusion proteins without such linkers. The increase in molar specific activity of fusion proteins in which the Factor VII/VIIa moiety is fused to the N-terminus of albumin via a peptidic linker compared to corresponding fusion proteins without such linker is at least 25%, preferably at least 50% and most preferred at least 100%. These linker bearing Factor VII/VIIa albumin fusion polypeptides also exhibit increased functional half-life in vivo as compared to wild-type FVIIa. However, chemical linkers or linker systems like without limitation avidin-biotin will function similarly as long as comparable distances are introduced between the Factor VII/FVIIa moiety and the albumin moiety. Below the term "linker peptide" or the like shall comprise such other functional linker means, whenever suitable.

The invention encompasses therapeutic Factor VII/VIIa polypeptides linked to the N-terminus of albumin, compositions, pharmaceutical compositions, formulations and kits. The invention also encompasses the use of said therapeutic albumin linked polypeptides in certain medical indications.

The invention also encompasses nucleic acid molecules encoding the albumin linked polypeptides of the invention, as well as vectors containing these nucleic acids, host cells transformed with these nucleic acids and vectors, and methods of making the albumin linked polypeptides of the invention using these nucleic acids, vectors, and/or host cells.

The invention also provides a composition comprising a Factor VII/FVIIa linked albumin polypeptide comprising a Factor VII or Factor VIIa peptide, or a fragment or variant thereof, optionally a peptidic linker, and albumin, or a fragment or variant thereof, and a pharmaceutically acceptable carrier. Another object of the invention is to provide a method of treating patients with bleeding disorders. The method comprises the step of administering an effective amount of the FVII/FVIIa linked albumin polypeptide.

Another object of the invention is to provide a nucleic acid molecule comprising a polynucleotide sequence encoding a Factor VII/VIIa linked albumin polypeptide comprising a Factor VII or Factor VIIa peptide, or a fragment or variant thereof, optionally a peptidic linker, and albumin, or a fragment or variant thereof, as well as a vector that comprises such a nucleic acid molecule. Said nucleic acid sequence encoding the fusion protein is located at the 3' end of a nucleic acid sequence encoding a propeptide mediating the gamma carboxylation of the Factor VII/VIIa fusion part.

The invention also provides a method for manufacturing a Factor VII/FVIIa linked albumin polypeptide comprising a Factor VII or Factor VIIa peptide, or a fragment or variant thereof, a peptidic linker, and albumin, or a fragment or variant thereof, wherein the method comprises:
(a) providing a nucleic acid comprising a nucleotide sequence encoding the Factor VII/VIIa linked albumin polypeptide expressible in a mammalian cell;
(b) expressing the nucleic acid in the organism to form a Factor VII/VIIa linked albumin polypeptide; and
(c) purifying the Factor VII/VIIa linked albumin polypeptide.

In one aspect the present invention relates to albumin fusion polypeptides and methods of treating, preventing, or ameliorating diseases or disorders. As used herein, "Factor VII/VIIa albumin fusion polypeptide" refers to a polypeptide formed by the fusion of at least one molecule of Factor VII/VIIa (or fragment or variant thereof) to the N-terminus of at least one molecule of albumin (or a fragment or variant thereof) both moieties being optionally separated via a peptidic linker.

A Factor VII/FVIIa albumin fusion polypeptide of the invention comprises at least a fragment or variant of a Factor VII/FVIIa and at least a fragment or variant of human serum albumin, which are associated with one another, such as by genetic fusion (i.e. the albumin fusion polypeptide is generated by translation of a nucleic acid in which a polynucleotide encoding all or a portion of a Factor VII/FVIIa is joined in-frame to the 5'end of a polynucleotide encoding all or a portion of albumin optionally linked by a polynucleotide which encodes a linker sequence, introducing a linker peptide between the Factor VII/VIIa moiety and the albumin moiety).

In one embodiment, the invention provides a Factor VII/VIIa albumin fusion polypeptide comprising, or alternatively consisting of biologically active and/or therapeutically active Factor VII/VIIa fused to the N-terminus of a serum albumin polypeptide.

In other embodiments, the invention provides an albumin fusion polypeptide comprising, or alternatively consisting of, a biologically active and/or therapeutically active fragment of Factor VII/VIIa and a peptidic linker fused to the N-terminus of a serum albumin protein.

In other embodiments, the invention provides a Factor VII/VIIa albumin fusion polypeptide comprising, or alternatively consisting of, a biologically active and/or therapeutically active variant of a Factor VII/VIIa fused to the N-terminus of a serum albumin polypeptide and optionally a peptidic linker.

In further embodiments, the invention provides a Factor VII/FVIIa albumin fusion polypeptide comprising, or alternatively consisting of, a biologically active and/or therapeutically active fragment or variant of a FVII/FVIIa fused to the N-terminus of a fragment or variant of serum albumin and optionally a peptidic linker.

In some embodiments, the invention provides an albumin fusion polypeptide comprising, or alternatively consisting of, the mature portion of a FVII/FVIIa fused to the N-terminus of the mature portion of serum albumin and optionally a peptidic linker.

According to WO 01/79271 an albumin fusion polypeptide comprising FVII/FVIIa can be used as a therapeutic in the indications "bleeding disorders", "hemophilia A and B", "liver disorders" and "surgery related hemorrhagic episodes".

It is another aspect of the invention that an albumin fusion polypeptide comprising FVII/FVIIa can be also used therapeutically in other indications. Most preferred indications are "bleeding episodes and surgery in patients with inherited or acquired hemophilia with inhibitors to coagulation Factors (FVIII or FIX)", "reversal of hemostasis deficits developed as consequence of drug treatments such as anti-platelet drugs or anti-coagulation drugs", "improvement of secondary hemostasis", "hemostasis deficits developed during infections or during illnesses such as Vitamin K deficiency or severe liver disease", "liver resection", "hemostasis deficits developed as consequences of snake bites", "gastro intestinal bleeds", "trauma", "consequences of massive transfusion (dilutional coagulopathy)", "coagulation factor deficiencies other than FVIII and FIX", "VWD", "FI deficiency", "FV deficiency", "FVII deficiency", "FX deficiency", "FXIII deficiency", "HUS", "inherited or acquired platelet diseases and disorders like thrombocytopenia, ITP, TTP, HELLP syndrome, Bernard-Soulier syndrome, Glanzmann Thrombasthenia, HIT", "Chediak-Higahi Syndrom", "Hermansky-Pudlak-Syndrome", "Rendu-Osler Syndrome", "Henoch-Schonlein purpura" and "Wound Healing".

DETAILED DESCRIPTION OF THE INVENTION

It is an object of the present invention to provide human Factor VII and human Factor VIIa or fragments or variants thereof fused to the N-terminus of human albumin or fragments or variants thereof with a longer functional half-life in vivo as compared to human Factor VII and human Factor VIIa or fragments or variants thereof. It is another object of the invention to provide human Factor VII and human Factor VIIa or fragments or variants thereof fused to the N-terminus of human albumin or fragments or variants with increased molar specific activity. To achieve this goal fusions of Factor VII or Factor VIIa to the N-terminus of serum albumin are provided optionally with an intervening peptidic linker between FVII/FVIIa and albumin.

The terms, human serum albumin (HSA) and human albumin (HA) are used interchangeably herein. The terms, "albumin" and "serum albumin" are broader, and encompass human serum albumin (and fragments and variants thereof) as well as albumin from other species (and fragments and variants thereof). Instead of albumin also other albumin-like proteins, like without limitation human alpha-fetoprotein (as described in WO 2005/024044) as well as their functional fragments or variants may be used.

As used herein, "albumin" refers collectively to albumin polypeptide or amino acid sequence, or an albumin fragment or variant, having one or more functional activities (e.g., biological activities) of albumin. In particular, "albumin" refers to human albumin or fragments thereof especially the mature form of human albumin as shown in SEQ ID No:22 herein or albumin from other vertebrates or fragments thereof, or analogs or variants of these molecules or fragments thereof.

The albumin portion of the albumin linked polypeptides may comprise the full length of the HA sequence as described above, or may include one or more fragments thereof that are capable of stabilizing or prolonging the therapeutic activity. Such fragments may be of 10 or more amino acids in length or may include about 15, 20, 25, 30, 50, or more contiguous amino acids from the HA sequence or may include part or all of the domains of HA.

The albumin portion of the albumin-linked polypeptides of the invention may be a variant of normal HA. The Factor VII protein portion of the albumin-linked polypeptides of the invention may also be variants of the Factor VII polypeptides as described herein. The term "variants" includes insertions, deletions and substitutions, either conservative or non-conservative, where such changes do not substantially alter the active site, or active domain, which confers the therapeutic activities of the Factor VII polypeptides In particular, the albumin-linked polypeptides of the invention may include naturally occurring polymorphic variants of human albumin and fragments of human albumin. The albumin may be derived from any vertebrate, especially any mammal, for example human, cow, sheep, or pig. Non-mammalian albumins include, but are not limited to, hen and salmon. The albumin portion of the albumin-linked polypeptide may be from a different animal than the FVII/FVIIa portion.

Generally speaking, an albumin fragment or variant will be at least 20, preferably at least 40, most preferably more than 70 amino acids long. The albumin variant may preferentially consist of or alternatively comprise at least one whole domain of albumin or fragments of said domains, for example domains 1 (amino acids 1-194 of SEQ ID NO:22), 2 (amino acids 195-387 of SEQ ID NO:22), 3 (amino acids 388-585 of SEQ ID NO:22), 1+2 (1-387 of SEQ ID NO:22), 2+3 (195-585 of SEQ ID NO:22) or 1+3 (amino acids 1-194 of SEQ ID NO:22+amino acids 388-585 of SEQ ID NO:22). Each domain is itself made up of two homologous subdomains namely 1-105, 120-194, 195-291, 316-387, 388-491 and 512-585, with flexible inter-subdomain linker regions comprising residues Lys106 to Glu119, Glu292 to Val315 and Glu492 to Ala511.

The albumin portion of an albumin fusion polypeptide of the invention may comprise at least one subdomain or domain of HA or conservative modifications thereof.

The invention relates to a modified Factor VII or Factor VIIa polypeptide, comprising linking the Factor VII or Factor VIIa polypeptide or fragment or variant thereof to the N-terminus of an albumin polypeptide or fragment or variant thereof optionally such that an intervening peptidic linker is introduced between the modified Factor VII or Factor VIIa and albumin such that the modified Factor VII or Factor VIIa polypeptide has an increased functional half-life in vivo compared to the Factor VII or Factor VIIa polypeptide which has not been linked to albumin or such that the molar specific activity of FVII/FVIIa fused to albumin with an intervening peptidic linker is higher than the molar specific activity of FVII/FVIIa fused to albumin without an intervening peptidic linker.

"Factor VII/VIIa" as used in this application means a therapeutic polypeptide consisting of either the nonactivated form (Factor VII) or the activated form (Factor VIIa) or mixtures thereof. "Factor VII/VIIa" within the above definition includes polypeptides that have the amino acid sequence of native human Factor VII/VIIa. It also includes polypeptides with a slightly modified amino acid sequence, for instance, a modified N-terminal or C-terminal end including terminal amino acid deletions or additions as long as those polypeptides substantially retain the biological activity of Factor VIIa. "Factor VII" within the above definition also includes natural allelic variations that may exist and occur from one individual to another. "Factor VII" within the above definition further includes variants of FVII/FVIIa. Such variants differ in one or more amino acid residues from the wild type sequence. Examples of such differences may include truncation of the N- and/or C-terminus by one or more amino acid residues (e.g. 1 to 10 amino acid residues), or addition of one or more extra residues at the N- and/or C-terminus, as well as conservative amino acid substitutions, i.e. substitutions performed within groups of amino acids with similar characteristics, e.g. (1) small amino acids, (2) acidic amino acids, (3) polar amino acids, (4) basic amino acids, (5) hydrophobic amino acids, and (6) aromatic amino acids. Examples of such conservative substitutions are shown in the following table.

TABLE 1

| | | | | |
|---|---|---|---|---|
| (1) | Alanine | Glycine | | |
| (2) | Aspartic acid | Glutamic acid | | |
| (3a) | Asparagine | Glutamine | | |
| (3b) | Serine | Threonine | | |
| (4) | Arginine | Histidine | Lysine | |
| (5) | Isoleucine | Leucine | Methionine | Valine |
| (6) | Phenylalanine | Tyrosine | Tryptophane | |

The fusion proteins display at least 25%, preferably more than 40%, even more preferably more than 70% and most preferably more than 90% of the molar specific activity of the unfused wild-type Factor VII/VIIa or respective FVII/FVIIa fragment or variant thereof.

The FVII/VIIa polypeptide of the invention linked via an intervening peptidic linker to the N-terminus of albumin has an increased molar specific activity as compared to the molar specific activity of a homologous Factor VII/VIIa albumin fusion without an intervening peptidic linker. The increase in molar specific activity of the albumin linked Factor VII/VIIa polypeptide of the invention as compared to the molar specific activity of a Factor VII/VIIa albumin fusion without an intervening peptidic linker is at least 25%, preferably at least 50%, more preferably at least 100% and most preferably at least 200%. The activity of Factor VII/VIIa is the ability to convert the substrate Factor X to the active Factor Xa. The FVIIa activity of a Factor VII/VIIa linked albumin polypeptide may be preferably measured using STACLOT®. Molar specific activity as used in this invention means: Activity as measured in STACLOT® assay after activation of the FVII linked albumin fusion protein in International Units (IU) per 100 IU of Factor VII/VIIa antigen as measured by ELISA.

The FVII/FVIIa albumin linked polypeptides of the invention have at least 25% higher molar specific activity compared to Factor VII/FVIIa albumin fusion without intervening peptidic linker and exhibit an increased functional half-life in vivo compared to the non-linked form of the Factor VII or Factor VIIa polypeptide. The functional half-life in vivo can be determined as shown in Lindley et al. (Pharmacokinetics and pharmacodynamics of recombinant Factor VIIa, Clin. Pharmacol Ther. (1994) 55:638-648)

The FVII/FVIIa albumin linked polypeptides of the invention have at least 25% higher molar specific activity compared to Factor VII/FVIIa albumin fusion proteins without intervening peptidic linker and their functional half-life in vivo is usually increased by at least 100%, preferably by at least 200%, even more preferably by at least 500% compared to the non-linked form of the Factor VII or Factor VIIa polypeptide.

One embodiment of the invention are therefore FVII/FVIIa albumin linked polypeptides have a peptidic linker consisting of at least one amino acid, preferably at least 3 amino acids more preferably at least 7 amino acids and most preferably at least 25 amino acids.

The functional half-life in vivo of the wild type form of human Factor VII is approximately 4 hours in humans. The functional half life of the Factor VII albumin linked polypeptides of the invention is usually at least about 8 hours, preferably at least about 12 hours, more preferably at least about 24 hours.

The functional half-life in vivo of the wild type form of human Factor VIIa is approximately 2 hours in humans. The functional half life of the Factor VIIa linked albumin polypeptides of the invention is usually at least about 4 hours, preferably at least about 6 hours, more preferably at least about 12 hours.

According to the invention the Factor VII/VIIa moiety is coupled to the albumin moiety by a peptidic linker. The linker is preferably flexible and non-immunogenic and generates a distance between human albumin and FVII/FVIIa which minimizes potential interference of the two fusion partners, resulting in an increased FVII/FVIIa activity of the fusion protein. Exemplary linkers include $(GGGGG)_N$ (SEQ ID NO: 56)$_N$ or $(GGGS)_N$ (SEQ ID NO: 57)$_N$ or $(GGS)_N$ (SEQ ID NO: 58)$_N$, wherein N is any integer greater than or equal to 1 and wherein G represents glycine and S represents serine. These amino acids belong to the group of natural amino acids and were chosen as examples for all possible natural amino acids.

In another embodiment of the invention the peptidic linker between the Factor VII/VIIa moiety and the albumin moiety contains consensus sites for the addition of posttranslational modifications. Preferably such modifications consist of glycosylation sites. More preferably, such modifications consist of at least one N-glycosylation site of the structure Asn-X-Ser/Thr, wherein X denotes any amino acid except proline. Even more preferably such N-glycosylation sites are inserted close to the amino and/or carboxy terminus of the peptidic linker such that they are capable to shield potential neoepitopes which might develop at the sequences where the Factor VII/VIIa moiety is transitioning into the peptidic linker and where the peptidic linker is transitioning into the albumin moiety sequence, respectively.

In another embodiment of the invention the peptidic linker between the Factor VII/VIIa moiety and the albumin moiety consists of peptide sequences, which serve as natural inter domain linkers in human proteins. Preferably such peptide sequences in their natural environment are located close to the protein surface and are accessible to the immune system so that one can assume a natural tolerance against this sequence. Examples are given in table 2.

TABLE 2

| Sequence | Protein | Accession No | Position of the linker |
|---|---|---|---|
| EPQ GGGGSGGGGSG E (SEQ ID NO: 47) | Protocadherin-10 | Q9P2E7 | close to membrane, extracellular |
| GGVGGGGGGAGI (SEQ ID NO: 48) | ANP Receptor | P17342 | extreme N-terminus, extracellular |
| PAR GGGGGG KAR (SEQ ID NO: 49) | Frizzled-8 | Q9H461 | inter-domain, secreted |
| GGPGGGGGGPGG (SEQ ID NO: 50) | Frizzled-8 | Q9H461 | C-terminus, secreted |
| TSR GGGGSGGG EPP (SEQ ID NO: 51) | LRRFN2 | Q9ULH4 | inter-domain, extracellular |

In yet another embodiment of the invention the peptidic linker between the Factor VII/VIIa moiety and the albumin moiety consists of peptide sequences, which are inter-domain linkers of known plasma proteins. Examples are given in table 3.

TABLE 3

| Sequence | Protein | Accession No | Position of the linker |
|---|---|---|---|
| MYGAKKPLNTEGVMKSRS (SEQ ID NO: 52) | FXIIIa | P00488 | between catalytic and Ig-like domain |
| RGEVKYPLCTRKESK (SEQ ID NO: 53) | FXIIIb | P05160 | between two Sushi domains |
| ESGGPLSLS (SEQ ID NO: 54) | FVIII | P00451 | within the B domain |
| APEAPPPTLPP (SEQ ID NO: 55) | vWF | P04275 | between two vWAs |

In yet another embodiment of the invention the Factor VII/VIIa moiety is coupled to the albumin moiety by a peptidic linker liberating the Factor VII/VIIa polypeptide at the site of coagulation wherein the linker contains a plasma protease cleavage site. Preferably such plasma protease cleavage sites are such of serine proteases. More preferably the cleavage site is from a coagulation protease cleavage site. Most preferably, the coagulation protease is selected from the group consisting of Factor IIa, Factor IXa, Factor Xa, Factor XIa, Factor XIIa, activated protein C, elastase or kallikrein. The amino acid sequences which are recognized and cleaved by these serine proteases are known to one of ordinary skill e.g. as described in "Hemostasis and Thrombosis, Basic Principles and Clinical Practice", Fourth Edition, Colman et al. 2001. Factor IIa: p34-35, p176, Factor IXa: p40-41, Factor Xa: p34-35, Factor XIa p128-129, Factor XIIa: p194, aPC: p34-35, p159, kallikrein: p103-104 or elastase (O'Reilly et al., 1999; Antiangiogenic activity of the cleaved conformation of the serpin antithrombin: Science 285:1926-1928).

The invention further relates to modified Factor VII/VIIa albumin fusion polypeptides according to the invention comprising additional modifications within the Factor VII/VIIa moiety.

In particular modifications of Factor VII/FVIIa are encompassed by the invention in which Factor VII/VIIa has been modified between Arg144 and Arg152 polypeptide by adding at least part of an activation peptide of a different vitamin K-dependent polypeptide or by replacing at least part of the putative activation peptide of a Factor VII/FVIIa polypeptide with at least part of an activation peptide of a different vitamin K-dependent polypeptide as described in the European patent application 04019485.4 (which is incorporated in this application by reference) and which is described in the following paragraph.

FVII is particular closely related to other Gla domain proteins like FIX, FX and protein C in which the N-terminal Gla domain is followed by two epidermal growth Factor (EGF) domains followed by the trypsin-type serine protease domain. Striking is the large difference in plasma half life of these closely related plasma proteins:

| | |
|---|---|
| FVII | 2-4 hours |
| Protein C: | 6-8 hours |
| FIX: | 18-30 hours |
| FX: | 20-42 hours |

The molecules are highly conserved, the most striking difference being within the activation domain. For FVII no activation peptide has been described. However, during activation FVII might in addition to cleavage at Arg152 also be cleaved at Arg144, then resulting in the release of a putative activation peptide of 8 amino acids containing a conserved N-glycosylation site. The sequence between Arg144 and Arg152 is called in the European patent application 04019485.4 "putative activation peptide".

Surprisingly the length of the activation peptides and post-translational modifications of the activation peptides correlate with increased half-life:

TABLE 4

| | Plasma half-life | Length of activation peptide within the respective human proteins | N-glycosylation sites within respective activation peptide |
|---|---|---|---|
| FVII | 2-4 hours | No activation peptide (or putative 8 amino acid activation peptide) | 1 in putative 8 amino acid activation peptide |
| Protein C | 6-8 hours | 16 amino acids | 0 |
| FIX | 18-30 hours | 34 amino acids | 2 |
| FX | 20-42 hours | 51 amino acids | 2 |

The invention therefore relates to a method for preparing a modified Factor VII/VIIa polypeptide linked to albumin, comprising modifying the Factor VII/VIIa polypeptide in the region between Arg144 and Arg152 such that the modified Factor VII/VIIa polypeptide has an increased half-life compared to the Factor VII/VIIa polypeptide in which this region has not been modified.

The invention further relates to a method for preparing such a modified Factor VII/VIIa linked albumin polypeptide, comprising modifying the Factor VII/VIIa polypeptide in the region between Arg144 and Arg152 of said Factor VII/VIIa linked albumin polypeptide by adding at least part of an activation peptide of a second vitamin K-dependent polypeptide or by replacing at least part of the putative activation peptide of a Factor VII/VIIa polypeptide with at least part of an activation peptide of a different vitamin K-dependent polypeptide.

The invention further encompasses additional mutations within the Factor VII/VIIa polypeptide sequence, which enhance catalytic activity, extend plasma half-life or modify Tissue Factor interaction. Particularly useful Factor VII mutations are described in Shah et al. (1998) Proc. Natl. Acad. Sci. USA 95:4229-4234, in which enhancements in protein function were reported. Other useful Factor VII/VIIa mutations are recited in the description of the prior art of European patent application 04019485.4.

The invention further relates to a polynucleotide encoding a Factor VII/VIIa albumin fusion polypeptide as described in this application. The term "polynucleotide(s)" generally refers to any polyribonucleotide or polydeoxyribonucleotide that may be unmodified RNA or DNA or modified RNA or DNA. The polynucleotide may be single- or double-stranded DNA, single or double-stranded RNA. As used herein, the term "polynucleotide(s)" also includes DNAs or RNAs that comprise one or more modified bases and/or unusual bases, such as inosine. It will be appreciated that a variety of modifications may be made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells.

The skilled person will understand that, due to the degeneracy of the genetic code, a given polypeptide can be encoded by different polynucleotides. These "variants" are encompassed by this invention.

Preferably, the polynucleotide of the invention is an isolated polynucleotide. The term "isolated" polynucleotide refers to a polynucleotide that is substantially free from other nucleic acid sequences, such as and not limited to other chromosomal and extrachromosomal DNA and RNA. Isolated polynucleotides may be purified from a host cell. Conventional nucleic acid purification methods known to skilled artisans may be used to obtain isolated polynucleotides. The term also includes recombinant polynucleotides and chemically synthesized polynucleotides.

Yet another aspect of the invention is a plasmid or vector comprising a polynucleotide according to the invention. Preferably, the plasmid or vector is an expression vector. In a particular embodiment, the vector is a transfer vector for use in human gene therapy.

Still another aspect of the invention is a host cell comprising a polynucleotide of the invention or a plasmid or vector of the invention.

The host cells of the invention may be employed in a method of producing a FVII/VIIa albumin fusion polypeptide, which is part of this invention. The method comprises:
culturing host cells of the invention under conditions such that the FVII/VIIa albumin fusion polypeptide is expressed; and
optionally recovering the FVII/VIIa albumin fusion polypeptide from the culture medium.

Expression of the Proposed Variants:

The production of recombinant proteins at high levels in suitable host cells requires the assembly of the above-mentioned modified cDNAs into efficient transcriptional units together with suitable regulatory elements in a recombinant expression vector, that can be propagated in various expression systems according to methods known to those skilled in the art. Efficient transcriptional regulatory elements could be derived from viruses having animal cells as their natural hosts or from the chromosomal DNA of animal cells. Preferably, promoter-enhancer combinations derived from the Simian Virus 40, adenovirus, BK polyoma virus, human cytomegalovirus, or the long terminal repeat of Rous sarcoma virus, or promoter-enhancer combinations including strongly constitutively transcribed genes in animal cells like beta-actin or GRP78 can be used. In order to achieve stable high levels of mRNA transcribed from the cDNAs, the transcriptional unit should contain in its 3'-proximal part a DNA region encoding a transcriptional termination-polyadenylation sequence. Preferably, this sequence is derived from the Simian Virus 40 early transcriptional region, the rabbit beta-globin gene, or the human tissue plasminogen activator gene.

The cDNAs are then integrated into the genome of a suitable host cell line for expression of the Factor VII/VIIa albumin fusion polypeptides. Preferably this cell line should be an animal cell-line of vertebrate origin in order to ensure correct folding, γ-carboxylation of glutamic acid residues within the Gla-domain, disulfide bond formation, asparagine-linked glycosylation, O-linked glycosylation, and other post-translational modifications as well as secretion into the cultivation medium. Examples of other post-translational modifications are tyrosine O-sulfation, hydroxylation, proteolytic processing of the nascent polypeptide chain and cleavage of the propeptide region. Examples of cell lines that can be used are monkey COS-cells, mouse L-cells, mouse C127-cells, hamster BHK-21 cells, human embryonic kidney 293 cells, and preferentially hamster CHO-cells.

The recombinant expression vector encoding the corresponding cDNAs can be introduced into an animal cell line in several different ways. For instance, recombinant expression vectors can be created from vectors based on different animal viruses. Examples of these are vectors based on baculovirus, vaccinia virus, adenovirus, and preferably bovine papilloma virus.

The transcription units encoding the corresponding DNA's can also be introduced into animal cells together with another recombinant gene which may function as a dominant selectable marker in these cells in order to facilitate the isolation of specific cell clones which have integrated the recombinant DNA into their genome. Examples of this type of dominant selectable marker genes are Tn5 amino glycoside phosphotransferase, conferring resistance to geneticin (G418), hygromycin phosphotransferase, conferring resistance to hygromycin, and puromycin acetyl transferase, conferring resistance to puromycin. The recombinant expression vector encoding such a selectable marker can reside either on the same vector as the one encoding the cDNA of the desired protein, or it can be encoded on a separate vector which is simultaneously introduced and integrated to the genome of the host cell, frequently resulting in a tight physical linkage between the different transcription units.

Other types of selectable marker genes, which can be used together with the cDNA of the desired protein, are based on various transcription units encoding dihydrofolate reductase (dhfr). After introduction of this type of gene into cells lacking endogenous dhfr-activity, preferentially CHO-cells (DUKX-B11, DG44) it will enable these to grow in media lacking nucleosides. An example of such a medium is Ham's F12 without hypoxanthine, thymidin, and glycine. These dhfr-genes can be introduced together with the coagulation Factor cDNA transcriptional units into CHO-cells of the above type, either linked on the same vector or on different vectors, thus creating dhfr-positive cell lines producing recombinant protein.

If the above cell lines are grown in the presence of the cytotoxic dhfr-inhibitor methotrexate, new cell lines resistant to methotrexate will emerge. These cell lines may produce recombinant protein at an increased rate due to the amplified number of linked dhfr and the desired protein's transcriptional units. When propagating these cell lines in increasing concentrations of methotrexate (1-10000 nM), new cell lines can be obtained which produce the desired protein at very high rate.

The above cell lines producing the desired protein can be grown on a large scale, either in suspension culture or on various solid supports. Examples of these supports are micro carriers based on dextran or collagen matrices, or solid supports in the form of hollow fibres or various ceramic materials. When grown in cell suspension culture or on micro carriers the culture of the above cell lines can be performed either as a batch culture or as a perfusion culture with continuous production of conditioned medium over extended periods of time. Thus, according to the present invention, the above cell lines are well suited for the development of an industrial process for the production of the desired recombinant proteins The recombinant protein, which accumulates in the medium of secreting cells of the above types, can be concentrated and purified by a variety of biochemical and chromatographic methods, including methods utilizing differences in size, charge, hydrophobicity, solubility, specific affinity, etc. between the desired protein and other substances in the cell cultivation medium.

An example of such purification is the adsorption of the recombinant protein to a monoclonal antibody which is immobilised on a solid support. After desorption, the protein can be further purified by a variety of chromatographic techniques based on the above properties.

It is preferred to purify the Factor VII/VIIa linked albumin polypeptide of the present invention to ≥80% purity, more preferably ≥95% purity, and particularly preferred is a pharmaceutically pure state that is greater than 99.9% pure with respect to contaminating macromolecules, particularly other proteins and nucleic acids, and free of infectious and pyrogenic agents. Preferably, an isolated or purified FVII/VIIa linked albumin polypeptide of the invention is substantially free of other polypeptides.

The Factor VII/VIIa linked albumin polypeptides described in this invention can be formulated into pharmaceutical preparations for therapeutic use. The purified proteins may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", 3$^{rd}$ edition, Kibbe et al., Pharmaceutical Press (2000)). In particular, the pharmaceutical composition comprising the polypeptide variant of the invention may be formulated in lyophilized or stable soluble form. The polypeptide variant may be lyophilized by a variety of procedures known in the art. Lyophilized formulations are reconstituted prior to use by the addition of one or more pharmaceutically acceptable diluents such as sterile water for injection or sterile physiological saline solution.

Formulations of the composition are delivered to the individual by any pharmaceutically suitable means of administration. Various delivery systems are known and can be used to administer the composition by any convenient route. Preferentially the compositions of the invention are administered systemically. For systemic use, the albumin linked Factor VII/VIIa variants of the invention are formulated for parenteral (e.g. intravenous, subcutaneous, intramuscular, intraperitoneal, intracerebral, intrapulmonary, intranasal or transdermal) or enteral (e.g., oral, vaginal or rectal) delivery according to conventional methods. The most preferential route of administration is intravenous administration. The formulations can be administered continuously by infusion or by bolus injection. Some formulations encompass slow release systems.

The modified biologically active albumin linked Factor VII/VIIa polypeptides of the present invention are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, and mode of administration and has to be determined in preclinical and clinical trials for each respective indication.

The pharmaceutical composition of the invention may be administered alone or in conjunction with other therapeutic agents. These agents may be incorporated as part of the same pharmaceutical.

The various products of the invention are useful as medicaments. Accordingly, the invention relates to a pharmaceutical composition comprising a FVII/VIIa linked albumin polypeptide as described herein, a polynucleotide of the invention, or a plasmid or vector of the invention.

The modified DNA's of this invention may also be integrated into a transfer vector for use in the human gene therapy.

Another aspect of the invention is the use of a FVII/VIIa linked albumin polypeptide as described herein, of a polynucleotide of the invention, of a plasmid or vector of the invention, or of a host cell of the invention for the manufacture of a medicament for the treatment or prevention of bleeding disorders. Bleeding disorders include but are not limited to hemophilia A. In another embodiment of the invention, the treatment comprises human gene therapy.

The invention also concerns a method of treating an individual in one or more of the following indications: "bleeding episodes and surgery in patients with inherited or acquired hemophilia with inhibitors to coagulation Factors (FVIII or FIX)", "reversal of hemostasis deficits developed as consequence of drug treatments such as anti-platelet drugs or anti-coagulation drugs", "improvement of secondary hemostasis", "hemostasis deficits developed during infections or during illnesses such as Vitamin K deficiency or severe liver disease", "liver resection", "hemostasis deficits developed as consequences of snake bites", "gastro intestinal bleeds". Also preferred indications are "trauma", "consequences of massive transfusion (dilutional coagulopathy)", "coagulation factor deficiencies other than FVIII and FIX", "VWD", "FI deficiency", "FV deficiency", "FVII deficiency", "FX deficiency", "FXIII deficiency", "HUS", "inherited or acquired platelet diseases and disorders like thrombocytopenia, ITP, TTP, HELLP syndrome, Bernard-Soulier syndrome, Glanzmann Thrombasthenia, HIT", "Chediak-Higahi Syndrom", "Hermansky-Pudlak-Syndrome", "Rendu-Osler Syndrome", "Henoch-Schonlein purpura" and "Wound Healing". The method comprises administering to said individual an efficient amount of the FVII/VIIa linked albumin polypeptide as described herein. In another embodiment, the method comprises administering to the individual an efficient amount of the polynucleotide of the invention or of a plasmid or vector of the invention. Alternatively, the method may comprise administering to the individual an efficient amount of the host cells of the invention described herein.

DESCRIPTION OF TABLES AND DRAWINGS

FIG. 1:
The XhoI restriction site introduced at the site of the natural FVII stop codon by replacing TAG by TCG is underlined. The NotI site used for further construction is double underlined. The amino acid sequence of the Factor VII C-terminus is given in three letter code (boxed).

FIG. 2:
Outline of the linker sequences inserted between the C-terminus of Factor VII and the N-terminus of albumin in the various pFVII constructs. The thrombin cleavage site in pFVII-834 is underlined. The asparagines of the N-glycosylation sites are double underlined.

FIG. 3:
FVII albumin fusion proteins were activated by FXa and FVIIa activity was measured in a STACLOT® assay. The plot shows the activity of proteins with increasing linker length with respect to the protein without linker (derived from plasmid pFVII-974).

Figure 4:
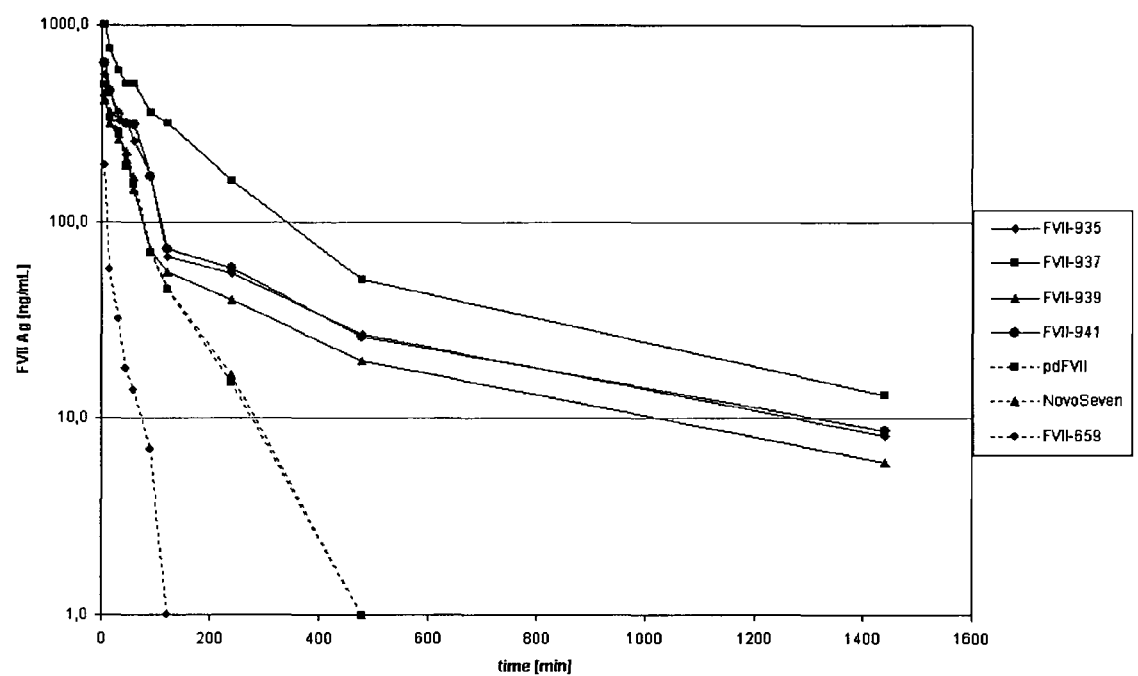

FIG. 4:
Results of PK experiments with wild-type Factor VII (pFVII-659), FVII albumin fusion proteins, plasma-derived FVII (pdFVII) and rFVIIa (NovoSeven®) as measured by ELISA.

EXAMPLES

Example 1

Generation of cDNAs Encoding FVII-Albumin Fusion Polypeptides

Factor VII coding sequence was amplified by PCR from a human liver cDNA library (ProQuest, Invitrogen) using primers We1303 and We1304 (SEQ ID NO 1 and 2). After a second round of PCR using primers We1286 and We 1287 (SEQ ID NO 3 and 4) the resulting fragment was cloned into pCR4TOPO (Invitrogen). From there the FVII cDNA was transferred as an EcoRI Fragment into the EcoRI site of pIRESpuro3 (BD Biosciences) wherein an internal XhoI site had been deleted previously. The resulting plasmid was designated pFVII-659.

Subsequently an XhoI restriction site was introduced into pFVII-659 at the site of the natural FVII stop codon (FIG. 1) by site directed mutagenesis according to standard protocols (QuickChange XL Site Directed Mutagenesis Kit, Stratagene) using oligonucleotides We1643 and We 1644 (SEQ ID NO 5 and 6). The resulting plasmid was designated pFVII-700.

Oligonucleotides We 1731 and We1732 (SEQ ID NO 7 and 8) were annealed in equimolar concentrations (10 pmol) under standard PCR conditions, filled up and amplified using a PCR protocol of a 2 min. initial denaturation at 94° C. followed by 7 cycles of 15 sec. of denaturation at 94° C., 15 sec. of annealing at 55° C. and 15 sec. of elongation at 72° C., and finalized by an extension step of 5 min at 72° C. The resulting fragment was digested with restriction endonucleases XhoI and NotI and ligated into pFVII-700 digested with the same enzymes. The resulting plasmid was designated pFVII-733, containing coding sequence for FVII and a C-terminal extension of a thrombin cleavable glycine/serine linker.

Based on pFVII-733 other linkers without thrombin cleavage site and additional N-glycosylation sites were inserted. For that primer pairs We2148 and We2149 (SEQ ID NO 9 and 10), We 2148 and We2150 (SEQ ID NO 9 and 11), We2148 and We2151 (SEQ ID NO 9 and 12), We2152 and We2153 (SEQ ID NO 13 and 14), We2152 and We2154 (SEQ ID NO 13 and 15), We2152 and 2155 (SEQ ID NO 13 and 16) and We2156 and We2157 (SEQ ID NO 17 and 18), respectively, were annealed and amplified as described above. The respective PCR fragments were digested with restriction endonucleases XhoI and BamH1 and inserted into pFVII-733 digested with the same enzymes. Into the BamH1 site of the resulting plasmids as well as into that of pFVII-733 a BamH1 fragment containing the cDNA of mature human albumin was inserted. This fragment had been generated by PCR on an albumin cDNA sequence using primers We1862 and We1902 (SEQ ID NO 19 and 20) under standard conditions. The final plasmids were designated pFVII-935, pFVII-936, pFVII-937, pFVII-938, pFVII-939, pFVII-940, pFVII-941 and pFVII-834, respectively. Their linker sequences and the C-terminal FVII and N-terminal albumin sequences are outlined in FIG. 2.

Based on pFVII-938 shorter linker sequences were generated by deletion mutagenesis. For this, mutagenesis primers We2247 and We2248 (SEQ ID No 23 and 24), We 2249 and We2250 (SEQ ID No 25 and 26), We 2251 and We2252 (SEQ ID No 27 and 28) and We2253 and We2254 (SEQ ID No 29 and 30) were used in standard mutagenesis protocols (Quick-Change XL Site Directed Mutagenesis Kit, Stratagene) to generate plasmids pFVII-1014, pFVII-1015, pFVII-1016 and pFVII-1370, respectively.

In order to generate a FVII albumin fusion protein without linker, deletion mutagenesis was applied as above upon plasmid pFVII-935 using primers We2181 and We2182 (SEQ ID NO 31 and 32). The resulting plasmid was designated pFVII-974.

Based on plasmid pFVII-974 insertion mutagenesis was applied to generate 1 to 3 amino acid linkers. For that mutagenesis primers We 2432 and We2433 (SEQ ID No 33 and 34), We2434 and We2435 (SEQ ID No 35 and 36) and We2436 and We2437 (SEQ ID No 37 and 38) were used in standard mutagenesis protocols (QuickChange XL Site Directed Mutagenesis Kit, Stratagene) to generate plasmids pFVII-1158, pFVII-1159 and pFVII-1160, respectively.

Further constructs were generated in analogous procedures, applying in standard mutagenesis protocols mutagenesis primers We2713 and We2714 (SEQ ID No 39 and 40) on plasmid pFVII-1370, We2715 and We2716 (SEQ ID No 41 and 42) on plasmid pFVII-1370, We2717 and We2718 (SEQ ID No 43 and 44) on plasmid pFVII-1016 and We2756 and We2757 (SEQ ID No 45 and 46) on plasmid pFVII-935 to generate plasmids pFVII-1361, pFVII-1362, pFVII-1363 and pFVII-1382, respectively.

The linker sequences and the C-terminal FVII and N-terminal albumin sequences of the above described plasmids are outlined in FIG. 2.

Example 2

Transfection and Expression of Factor VII-Albumin Fusion Polypeptides

Plasmids were grown up in *E. coli* TOP10 (Invitrogen) and purified using standard protocols (Qiagen). HEK-293 cells were transfected using the Lipofectamine 2000 reagent (Invitrogen) and grown up in serum-free medium (Invitrogen 293 Express) in the presence of 50 ng/ml Vitamin K and 4 µg/ml Puromycin. Transfected cell populations were spread through T-flasks into roller bottles from which supernatant was harvested for purification.

Example 3

Purification of FVII and FVII-Albumin Fusion Polypeptides

Cell culture harvest containing FVII or FVII albumin fusion protein was applied on a 2.06 mL Q-Sepharose FF column previously equilibrated with 20 mM HEPES buffer pH 7.4. Subsequently, the column was washed with 10 volumes of the named HEPES buffer. Elution of the bound FVII molecules was achieved by running a linear gradient from 0 to 1.0 M NaCl in 20 mM HEPES buffer within 20 column volumes. The eluate contained about 85-90% of the applied FVII antigen at protein concentrations between 0.5 and 1 g/L.

Alternatively FVII was purified by chromatography using immobilized tissue factor as described in EP 0770625B1.

FVII antigen and activity were determined as described in example 4.

Example 4

Determination of FVII Activity and Antigen

FVII activity was determined using a commercially available chromogenic test kit (Chromogenix Coaset FVII using standard human plasma [Dade Behring] as standard) based on the method described by Seligsohn et al. Blood (1978) 52:978-988.

FVIIa activity was determined using a commercially available test kit (STACLOT®)VIIa-rTF, Diagnostica Stago) based on the method described by Morissey et al. (1993) Blood 81:734-744.

FVII antigen was determined by an ELISA whose performance is known to those skilled in the art. Briefly, microplates were incubated with 120 µL per well of the capture antibody (sheep anti human FVII IgG, Cedarlane CL20030AP, diluted 1:1000 in Buffer A [Sigma C3041]) overnight at ambient temperature. After washing plates three times with buffer B (Sigma P3563), each well was incubated with 200 µL buffer C (Sigma P3688) for one hour at ambient temperature. After another three wash steps with buffer B, serial dilutions of the test sample in buffer B as well as serial dilutions of standard human plasma (Dade Behring; 50-0.5 mU/mL [1 mU equals 0.5 ng]) in buffer B (volumes per well: 100 µL) were incubated for two hours at ambient temperature. After three wash steps with buffer B, 100 µL of a 1:5000 dilution in buffer B of the detection antibody (sheep anti human FVII IgG, Cedarlane CL20030K, peroxidase labelled) were added to each well and incubated for another two hours at ambient temperature. After three wash steps with buffer B, 100 µL of substrate solution (TMB, Dade Behring, OUVF) were added per well and incubated for 30 minutes at ambient temperature in the dark. Addition of 100 µL undiluted stop solution (Dade Behring, OSFA) prepared the samples for reading in a suitable microplate reader at 450 nm wavelength. Concentrations of test samples were then calculated using the standard curve with standard human plasma as reference.

Example 5

Activation of FVII and FVII-Albumin Fusion Polypeptides by Factor Xa

FVII polypeptides purified as described in example 3 were dialyzed against a buffer consisting of 20 mM HEPES, 150 mM NaCl, 1 mM Na-Citrate, 1 g/L Na-Caprylate pH 8.5. Within this buffer environment FVII was activated to FVIIa by incubation with FXa (commercially available preparation, 100 IU/mL, ERL), Phospholipid (Phospholipon 25P, 1 g/L, Rhone Poulenc-Nattermann, Köln) and $Ca^{++}$ ($CaCl_2$ solution in Aqua dest, 1M) for various time intervals at 37° C. The final concentrations were ~30 to 65 IU/mL FVII, measured by the chromogenic assay; 0.5% FXa related to FVII i.e. 1 IU FXa and 200 IU FVII, 0.02 g/L Phospholipid and 5 mM $CaCl_2$.

Activation was terminated by addition of 10% (v/v) of a buffer consisting of 20 mM HEPES, 150 mM NaCl, 200 mM Na-Citrate, 1 g/L Na-Caprylate pH 5.0.

To monitor the cleavage of the molecules in parallel a sample of the activation mixture and a corresponding non-activated sample were applied to SDS-PAGE, stained with Coomassie blue and scanned for band density.

Briefly, samples were reduced, applied to SDS-PAGE (Gradient 8-16% Polyacrylamid, Novex® Tris-Glycin Gels, Invitrogen; according to the manufactures instructions) and stained with Coomassie blue G-250. The resulting bands were scanned (Versa DOC®, Bio-Rad) and relative protein concentrations were calculated using the software Image Quant (V 4.20, Amersham).

Example 6

Activity of FVII-Albumin Fusion Proteins is Dependent on Linker Length

FVII-albumin fusion proteins with linker length between 0 and 31 amino acids were activated as described above and FVIIa activity was determined in a STACLOT® assay. Although the fusion polypeptides irrespective of linker length showed a comparable degree of FXa cleavage the FVIIa activities of the albumin fusion proteins measured by the activity assay showed a surprising result: the longer the linker between FVII and the albumin moiety became, the higher was the molar specific FVIIa activity measured (FIG. 3 and table 5) and the construct without linker (974) displayed less than half of the FVIIa activity compared to the constructs with linker peptides of 19 or more amino acids in length. Even one amino acid as linker (pFVII-1158) increased the molar specific activity of the fusion protein by 31% compared to a fusion protein without linker (pFVII-974). This strongly suggests that the direct fusion of FVII and albumin sequences might lead to a conformational situation where the albumin moiety interferes either with the conformation of its FVIIa part or its interaction with its substrate. This interference seems to be significantly reduced in the constructs having between Factor VII/VIIa and albumin an intervening peptidic linker.

The albumin fusion protein without linker (974) displayed about 25% of specific molar activity when compared to NovoSeven® (table 6).

TABLE 5

| Albumin fusion protein derived from pFVII- | linker length [amino acids] | no. of N-glycosylation sites within the linker | % increase in Staclot activity compared to a fusion protein without linker |
| --- | --- | --- | --- |
| 974 | 0 | 0 | 0 |
| 1158 | 1 | 0 | 31.3 |
| 1159 | 2 | 0 | 75.6 |
| 1160 | 3 | 0 | 104.0 |
| 1370 | 4 | 0 | 81.6 |
| 1361 | 5 | 0 | 107.0 |
| 1362 | 6 | 0 | 98.5 |
| 1363 | 7 | 0 | 178.1 |
| 1015 | 10 | 1 | 155.7 |
| 1014 | 13 | 2 | 201.5 |
| 1382 | 16 | 0 | 149.8 |
| 935 | 19 | 0 | 194.5 |
| 936 | 25 | 0 | 255.7 |
| 937 | 31 | 0 | 249.8 |

TABLE 6

Comparison of molar specific activity (expressed in FVIIa units measured by the Staclot assay per 100 units of FVII antigen determined by Elisa) between FVII albumin fusion protein without linker (974) and NovoSeven ®

| Protein | Specific Staclot activity [IU/100 IU FVII Antigen] | % specific activity |
| --- | --- | --- |
| 974 | 489 | 27.8 |
| NovoSeven ® | 1759 | 100.0 |

The invention claimed is:
1. An albumin fusion protein comprising:
   (a) Factor VII or Factor VIIa,
   (b) albumin, and
   (c) a peptide linker that joins the Factor VII or Factor VIIa to the N-terminus of the albumin,
wherein the peptide linker is at least 25 amino acids in length and comprises Ser-Ser-(Gly-Gly-Ser)$_n$-Gly-Ser, wherein n is an integer greater than or equal to 7.

2. The albumin fusion polypeptide of claim 1, wherein n is an integer greater than or equal to 9, and wherein the peptide linker is at least 31 amino acids in length.

3. The albumin fusion polypeptide of claim 1, wherein the linker comprises Ser-Ser-(Gly-Gly-Ser)$_n$-Gly-Ser, and n is 9.

4. The albumin fusion polypeptide of claim 1, wherein the linker comprises Ser-Ser-(Gly-Gly-Ser)$_n$-Gly-Ser, n is 9, and the peptide linker is 31 amino acids in length.

5. The albumin fusion polypeptide of claim 1, wherein the linker comprises at least one N-glycosylation site of the structure Asn-X-Ser/Thr, wherein X denotes any amino acid except proline.

6. The albumin fusion polypeptide of claim 1, wherein the albumin fusion polypeptide has a Factor VII/VIIa molar specific activity that is increased by at least 100% as compared to a Factor VII- or Factor VIIa-albumin fusion polypeptide without a linker.

7. The albumin fusion polypeptide of claim 1, wherein the albumin fusion polypeptide has increased functional plasma half-life in vivo as compared to an unfused Factor VII or Factor VIIa.

8. The albumin fusion polypeptide of claim 7, wherein the increased functional plasma half-life of the albumin fusion polypeptide is increased by at least 100% as compared to the unfused Factor VII or Factor VIIa.

9. The albumin fusion polypeptide of claim 1, wherein the peptide linker contains a protease cleavage site.

10. The albumin fusion polypeptide of claim 9, wherein the cleavage site can be cleaved by one or more of Factor IIa, Factor IXa, Factor Xa, Factor XIa, Factor XIIa, activated protein C, elastase, or kallikrein.

11. The albumin fusion polypeptide of claim 1, wherein the albumin fusion polypeptide is modified to comprise an activation peptide from a vitamin K-dependent polypeptide that is not Factor VII or Factor VIIa.

12. The albumin fusion polypeptide of claim 1, wherein the Factor VII or Factor VIIa has procoagulant activity.

13. A pharmaceutical composition comprising the albumin fusion polypeptide of claim 1 and a pharmaceutically acceptable carrier or excipient.

* * * * *

UNITED STATES PATENT AND TRADEMARK OFFICE
CERTIFICATE OF CORRECTION

PATENT NO. : 8,765,915 B2  
APPLICATION NO. : 12/223616  
DATED : July 1, 2014  
INVENTOR(S) : Weimer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 517 days.

Signed and Sealed this  
Fourth Day of August, 2015

Michelle K. Lee  
*Director of the United States Patent and Trademark Office*

SEQUENCE LISTING

```
<160> NUMBER OF SEQ ID NOS: 58

<210> SEQ ID NO 1
<211> LENGTH: 19
<212> TYPE: DNA
<213> ORGANISM: Artificial
<220> FEATURE:
<223> OTHER INFORMATION: Primer

<400> SEQUENCE: 1
ggcaggggca gcactgcag                                                 19

<210> SEQ ID NO 2
<211> LENGTH: 19
<212> TYPE: DNA
<213> ORGANISM: Artificial
<220> FEATURE:
<223> OTHER INFORMATION: Primer

<400> SEQUENCE: 2
cacaggccag ggctgctgg                                                 19

<210> SEQ ID NO 3
<211> LENGTH: 27
<212> TYPE: DNA
<213> ORGANISM: Artificial
<220> FEATURE:
<223> OTHER INFORMATION: Primer
```

```
<400> SEQUENCE: 3
gcggctagca tggtctccca ggccctc                                         27

<210> SEQ ID NO 4
<211> LENGTH: 30
<212> TYPE: DNA
<213> ORGANISM: Artificial
<220> FEATURE:
<223> OTHER INFORMATION: Primer

<400> SEQUENCE: 4
gcggcggccg cctagggaaa tggggctcgc                                      30

<210> SEQ ID NO 5
<211> LENGTH: 33
<212> TYPE: DNA
<213> ORGANISM: Artificial
<220> FEATURE:
<223> OTHER INFORMATION: Primer

<400> SEQUENCE: 5
gagccccatt tccctcgagg gccgccgcaa ggg                                  33

<210> SEQ ID NO 6
<211> LENGTH: 33
<212> TYPE: DNA
<213> ORGANISM: Artificial
<220> FEATURE:
<223> OTHER INFORMATION: Primer

<400> SEQUENCE: 6
cccttgcggc ggccctcgag ggaaatgggg ctc                                  33

<210> SEQ ID NO 7
<211> LENGTH: 61
<212> TYPE: DNA
<213> ORGANISM: Artificial
<220> FEATURE:
<223> OTHER INFORMATION: Primer

<400> SEQUENCE: 7
gtggtgctcg agcgtgcccc gcgccgtggg cggctccggc ggctccggcg gctccggatc     60
c                                                                     61

<210> SEQ ID NO 8
<211> LENGTH: 62
<212> TYPE: DNA
<213> ORGANISM: Artificial
<220> FEATURE:
<223> OTHER INFORMATION: Primer

<400> SEQUENCE: 8
caccacgcgg ccgcttatca ggatccggag ccgccggagc cgccggagcc gcccacggcg     60
cg                                                                    62

<210> SEQ ID NO 9
<211> LENGTH: 52
<212> TYPE: DNA
<213> ORGANISM: Artificial
<220> FEATURE:
<223> OTHER INFORMATION: Primer

<400> SEQUENCE: 9
ctcgagcggg ggatctggcg ggtctggagg ctctggaggg tcgggaggct ct             52
```

```
<210> SEQ ID NO 10
<211> LENGTH: 37
<212> TYPE: DNA
<213> ORGANISM: Artificial
<220> FEATURE:
<223> OTHER INFORMATION: Primer

<400> SEQUENCE: 10
ggatccagag cctcccgacc ctccagagcc tccagac                              37

<210> SEQ ID NO 11
<211> LENGTH: 46
<212> TYPE: DNA
<213> ORGANISM: Artificial
<220> FEATURE:
<223> OTHER INFORMATION: Primer

<400> SEQUENCE: 11
ggatccagat cccccagagc ctccagagcc tcccgaccct ccagag                    46

<210> SEQ ID NO 12
<211> LENGTH: 59
<212> TYPE: DNA
<213> ORGANISM: Artificial
<220> FEATURE:
<223> OTHER INFORMATION: Primer

<400> SEQUENCE: 12
ggatcccgac cctccagacc cgccagatcc cccagagcct ccagagcctc ccgaccctc      59

<210> SEQ ID NO 13
<211> LENGTH: 49
<212> TYPE: DNA
<213> ORGANISM: Artificial
<220> FEATURE:
<223> OTHER INFORMATION: Primer

<400> SEQUENCE: 13
ctcgagcaac ggatctggcg ggtctggagg ctctggaggg tcgggaggc                 49

<210> SEQ ID NO 14
<211> LENGTH: 40
<212> TYPE: DNA
<213> ORGANISM: Artificial
<220> FEATURE:
<223> OTHER INFORMATION: Primer

<400> SEQUENCE: 14
ggatccattg cctcccgacc ctccagagcc tccagacccg                           40

<210> SEQ ID NO 15
<211> LENGTH: 48
<212> TYPE: DNA
<213> ORGANISM: Artificial
<220> FEATURE:
<223> OTHER INFORMATION: Primer

<400> SEQUENCE: 15
ggatccgttt cccccagagc ctccagagcc tcccgaccct ccagagcc                  48

<210> SEQ ID NO 16
<211> LENGTH: 64
<212> TYPE: DNA
<213> ORGANISM: Artificial
<220> FEATURE:
<223> OTHER INFORMATION: Primer
```

<400> SEQUENCE: 16
ggatccgttc cctccagacc cgccagatcc cccagagcct ccagagcctc ccgaccctcc      60
agag                                                                  64

<210> SEQ ID NO 17
<211> LENGTH: 56
<212> TYPE: DNA
<213> ORGANISM: Artificial
<220> FEATURE:
<223> OTHER INFORMATION: Primer

<400> SEQUENCE: 17
ctcgagcaat ggatctggcg ggtctggagg ctctggaggg tcgaatggct ctggag         56

<210> SEQ ID NO 18
<211> LENGTH: 64
<212> TYPE: DNA
<213> ORGANISM: Artificial
<220> FEATURE:
<223> OTHER INFORMATION: Primer

<400> SEQUENCE: 18
ggatccgttc cctccagacc cgccagatcc cccagagcct ccagagccat cgaccctcc       60 agag                                                                  64

<210> SEQ ID NO 19
<211> LENGTH: 31
<212> TYPE: DNA
<213> ORGANISM: Artificial
<220> FEATURE:
<223> OTHER INFORMATION: Primer

<400> SEQUENCE: 19
gtgggatccg atgcacacaa gagtgaggtt g                                    31

<210> SEQ ID NO 20
<211> LENGTH: 35
<212> TYPE: DNA
<213> ORGANISM: Artificial
<220> FEATURE:
<223> OTHER INFORMATION: Primer

<400> SEQUENCE: 20
cacggatccc tataagccta aggcagcttg acttg                                35

<210> SEQ ID NO 21
<211> LENGTH: 406
<212> TYPE: PRT
<213> ORGANISM: Homo Sapiens

<400> SEQUENCE: 21

Ala Asn Ala Phe Leu Glu Glu Leu Arg Pro Gly Ser Leu Glu Arg Glu
1               5                  10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

```
Cys Glu Thr His Lys Asp Asp Gln Leu Ile Cys Val Asn Glu Asn Gly
            85                  90                  95

Gly Cys Glu Gln Tyr Cys Ser Asp His Thr Gly Thr Lys Arg Ser Cys
        100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405

<210> SEQ ID NO 22
<211> LENGTH: 585
<212> TYPE: PRT
<213> ORGANISM: Homo Sapiens

<400> SEQUENCE: 22

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45
```

```
Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460
```

```
Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu
        580                 585
```

<210> SEQ ID NO 23
<211> LENGTH: 26
<212> TYPE: DNA
<213> ORGANISM: Artificial
<220> FEATURE:
<223> OTHER INFORMATION: Primer

<400> SEQUENCE: 23
gagcaacgga tctggagggt cgggag                                         26

<210> SEQ ID NO 24
<211> LENGTH: 26
<212> TYPE: DNA
<213> ORGANISM: Artificial
<220> FEATURE:
<223> OTHER INFORMATION: Primer

<400> SEQUENCE: 24
ctcccgaccc tccagatccg ttgctc                                         26

<210> SEQ ID NO 25
<211> LENGTH: 26
<212> TYPE: DNA
<213> ORGANISM: Artificial
<220> FEATURE:
<223> OTHER INFORMATION: Primer

<400> SEQUENCE: 25
ctggcgggtc tggatccgat gcacac                                         26

<210> SEQ ID NO 26
<211> LENGTH: 26
<212> TYPE: DNA
<213> ORGANISM: Artificial
<220> FEATURE:
<223> OTHER INFORMATION: Primer

<400> SEQUENCE: 26
gtgtgcatcg gatccagacc cgccag                                         26

<210> SEQ ID NO 27
<211> LENGTH: 29
<212> TYPE: DNA
<213> ORGANISM: Artificial
<220> FEATURE:
<223> OTHER INFORMATION: Primer

<400> SEQUENCE: 27
cgagcaacgg atctggatcc gatgcacac         29

<210> SEQ ID NO 28
<211> LENGTH: 29
<212> TYPE: DNA
<213> ORGANISM: Artificial
<220> FEATURE:
<223> OTHER INFORMATION: Primer

<400> SEQUENCE: 28
gtgtgcatcg gatccagatc cgttgctcg         29

<210> SEQ ID NO 29
<211> LENGTH: 29
<212> TYPE: DNA
<213> ORGANISM: Artificial
<220> FEATURE:
<223> OTHER INFORMATION: primer

<400> SEQUENCE: 29
catttccctc gagcggatcc gatgcacac         29

<210> SEQ ID NO 30
<211> LENGTH: 29
<212> TYPE: DNA
<213> ORGANISM: Artificial
<220> FEATURE:
<223> OTHER INFORMATION: primer

<400> SEQUENCE: 30
gtgtgcatcg gatccgctcg agggaaatg         29

<210> SEQ ID NO 31
<211> LENGTH: 27
<212> TYPE: DNA
<213> ORGANISM: Artificial
<220> FEATURE:
<223> OTHER INFORMATION: Primer

<400> SEQUENCE: 31
ccccatttcc cgatgcacac aagagtg          27

<210> SEQ ID NO 32
<211> LENGTH: 27
<212> TYPE: DNA
<213> ORGANISM: Artificial
<220> FEATURE:
<223> OTHER INFORMATION: Primer

<400> SEQUENCE: 32
cactcttgtg tgcatcggga aatgggg          27

<210> SEQ ID NO 33
<211> LENGTH: 33
<212> TYPE: DNA
<213> ORGANISM: Artificial
<220> FEATURE:
<223> OTHER INFORMATION: primer

<400> SEQUENCE: 33
gccccatttc ccggggatgc acacaagagt gag    33

```
<210> SEQ ID NO 34
<211> LENGTH: 33
<212> TYPE: DNA
<213> ORGANISM: Artificial
<220> FEATURE:
<223> OTHER INFORMATION: primer

<400> SEQUENCE: 34
ctcactcttg tgtgcatccc cgggaaatgg ggc                            33

<210> SEQ ID NO 35
<211> LENGTH: 36
<212> TYPE: DNA
<213> ORGANISM: Artificial
<220> FEATURE:
<223> OTHER INFORMATION: primer

<400> SEQUENCE: 35
gccccatttc ccgggtccga tgcacacaag agtgag                         36

<210> SEQ ID NO 36
<211> LENGTH: 36
<212> TYPE: DNA
<213> ORGANISM: Artificial
<220> FEATURE:
<223> OTHER INFORMATION: primer

<400> SEQUENCE: 36
ctcactcttg tgtgcatcgg acccgggaaa tggggc                         36

<210> SEQ ID NO 37
<211> LENGTH: 39
<212> TYPE: DNA
<213> ORGANISM: Artificial
<220> FEATURE:
<223> OTHER INFORMATION: primer

<400> SEQUENCE: 37
gccccatttc ccgggggctc cgatgcacac aagagtgag                      39

<210> SEQ ID NO 38
<211> LENGTH: 39
<212> TYPE: DNA
<213> ORGANISM: Artificial
<220> FEATURE:
<223> OTHER INFORMATION: primer

<400> SEQUENCE: 38
ctcactcttg tgtgcatcgg agccccckggg aaatggggc                     39

<210> SEQ ID NO 39
<211> LENGTH: 29
<212> TYPE: DNA
<213> ORGANISM: Artificial
<220> FEATURE:
<223> OTHER INFORMATION: primer

<400> SEQUENCE: 39
cctcgagcgg agggtccgat gcacacaag                                 29

<210> SEQ ID NO 40
<211> LENGTH: 29
<212> TYPE: DNA
<213> ORGANISM: Artificial
<220> FEATURE:
<223> OTHER INFORMATION: primer
```

```
<400> SEQUENCE: 40
cttgtgtgca tcggaccctc cgctcgagg                                    29

<210> SEQ ID NO 41
<211> LENGTH: 32
<212> TYPE: DNA
<213> ORGANISM: Artificial
<220> FEATURE:
<223> OTHER INFORMATION: primer

<400> SEQUENCE: 41
cccatttccc tcgggggga gcggatccga tg                                 32

<210> SEQ ID NO 42
<211> LENGTH: 32
<212> TYPE: DNA
<213> ORGANISM: Artificial
<220> FEATURE:
<223> OTHER INFORMATION: primer

<400> SEQUENCE: 42
catcggatcc gctccccccc gagggaaatg gg                                32

<210> SEQ ID NO 43
<211> LENGTH: 35
<212> TYPE: DNA
<213> ORGANISM: Artificial
<220> FEATURE:
<223> OTHER INFORMATION: primer

<400> SEQUENCE: 43
cccatttccc tcgagcggcg gatctggatc cgatg                             35

<210> SEQ ID NO 44
<211> LENGTH: 35
<212> TYPE: DNA
<213> ORGANISM: Artificial
<220> FEATURE:
<223> OTHER INFORMATION: primer

<400> SEQUENCE: 44
catcggatcc agatccgccg ctcgagggaa atggg                             35

<210> SEQ ID NO 45
<211> LENGTH: 27
<212> TYPE: DNA
<213> ORGANISM: Artificial
<220> FEATURE:
<223> OTHER INFORMATION: primer

<400> SEQUENCE: 45
ggtcgggagg cgatgcacac aagagtg                                      27

<210> SEQ ID NO 46
<211> LENGTH: 27
<212> TYPE: DNA
<213> ORGANISM: Artificial
<220> FEATURE:
<223> OTHER INFORMATION: primer

<400> SEQUENCE: 46
cactcttgtg tgcatcgcct cccgacc                                      27
```

```
<210> SEQ ID NO 47
<211> LENGTH: 15
<212> TYPE: PRT
<213> ORGANISM: Artificial
<220> FEATURE:
<223> OTHER INFORMATION: Linker

<400> SEQUENCE: 47

Glu Pro Gln Gly Gly Gly Gly Ser Gly Gly Gly Ser Gly Glu
1               5                   10                  15

<210> SEQ ID NO 48
<211> LENGTH: 12
<212> TYPE: PRT
<213> ORGANISM: Artificial
<220> FEATURE:
<223> OTHER INFORMATION: Linker

<400> SEQUENCE: 48

Gly Gly Val Gly Gly Gly Gly Gly Gly Ala Gly Ile
1               5                   10

<210> SEQ ID NO 49
<211> LENGTH: 12
<212> TYPE: PRT
<213> ORGANISM: Artificial
<220> FEATURE:
<223> OTHER INFORMATION: Linker

<400> SEQUENCE: 49

Pro Ala Arg Gly Gly Gly Gly Gly Gly Lys Ala Arg
1               5                   10

<210> SEQ ID NO 50
<211> LENGTH: 13
<212> TYPE: PRT
<213> ORGANISM: Artificial
<220> FEATURE:
<223> OTHER INFORMATION: Linker

<400> SEQUENCE: 50

Gly Gly Pro Gly Gly Gly Gly Gly Gly Pro Gly Gly
1               5                   10

<210> SEQ ID NO 51
<211> LENGTH: 14
<212> TYPE: PRT
<213> ORGANISM: Artificial
<220> FEATURE:
<223> OTHER INFORMATION: Linker

<400> SEQUENCE: 51

Thr Ser Arg Gly Gly Gly Gly Ser Gly Gly Gly Glu Pro Pro
1               5                   10

<210> SEQ ID NO 52
<211> LENGTH: 18
<212> TYPE: PRT
<213> ORGANISM: Artificial
<220> FEATURE:
<223> OTHER INFORMATION: Linker

<400> SEQUENCE: 52

Met Tyr Gly Ala Lys Lys Pro Leu Asn Thr Glu Gly Val Met Lys Ser
1               5                   10                  15

Arg Ser
```

```
<210> SEQ ID NO 53
<211> LENGTH: 15
<212> TYPE: PRT
<213> ORGANISM: Artificial
<220> FEATURE:
<223> OTHER INFORMATION: Linker

<400> SEQUENCE: 53

Arg Gly Glu Val Lys Tyr Pro Leu Cys Thr Arg Lys Glu Ser Lys
1               5                   10                  15

<210> SEQ ID NO 54
<211> LENGTH: 9
<212> TYPE: PRT
<213> ORGANISM: Artificial
<220> FEATURE:
<223> OTHER INFORMATION: Linker

<400> SEQUENCE: 54

Glu Ser Gly Gly Pro Leu Ser Leu Ser
1               5

<210> SEQ ID NO 55
<211> LENGTH: 11
<212> TYPE: PRT
<213> ORGANISM: Artificial
<220> FEATURE:
<223> OTHER INFORMATION: Linker

<400> SEQUENCE: 55

Ala Pro Glu Ala Pro Pro Pro Thr Leu Pro Pro
1               5                   10

<210> SEQ ID NO 56
<211> LENGTH: 5
<212> TYPE: PRT
<213> ORGANISM: Artificial
<220> FEATURE:
<223> OTHER INFORMATION: Linker

<400> SEQUENCE: 56

Gly Gly Gly Gly Gly
1               5

<210> SEQ ID NO 57
<211> LENGTH: 4
<212> TYPE: PRT
<213> ORGANISM: Artificial
<220> FEATURE:
<223> OTHER INFORMATION: Linker

<400> SEQUENCE: 57

Gly Gly Gly Ser
1

<210> SEQ ID NO 58
<211> LENGTH: 3
<212> TYPE: PRT
<213> ORGANISM: Artificial
<220> FEATURE:
<223> OTHER INFORMATION: Linker

<400> SEQUENCE: 58

Gly Gly Ser
1
```